United States Patent [19]

Steuer et al.

[11] Patent Number: 4,504,263
[45] Date of Patent: Mar. 12, 1985

[54] FLOW RATE MONITOR WITH OPTICAL SENSING CHAMBER

[75] Inventors: Robert R. Steuer; David H. Harris, both of Salt Lake City, Utah

[73] Assignee: ValleyLab, Inc., Boulder, Colo.

[21] Appl. No.: 550,171

[22] Filed: Nov. 10, 1983

Related U.S. Application Data

[63] Continuation-in-part of Ser. No. 452,395, Dec. 22, 1982, abandoned.

[51] Int. Cl.³ .............................................. A61M 5/16
[52] U.S. Cl. ...................................... 604/65; 604/67; 128/DIG. 13
[58] Field of Search .................. 604/65, 67, 251, 253; 128/DIG. 13

[56] References Cited

U.S. PATENT DOCUMENTS

| | | |
|---|---|---|
| 3,390,577 | 7/1968 | Phelps et al. |
| 3,450,153 | 6/1969 | Hildebrandt et al. |
| 3,563,090 | 2/1971 | Deltour |
| 3,601,124 | 8/1971 | Petree |
| 3,624,800 | 11/1971 | Swick |
| 3,631,437 | 12/1971 | Campbell |
| 3,655,095 | 4/1972 | Kienitz |
| 3,736,930 | 6/1973 | Georgi |
| 3,790,042 | 2/1974 | McCormick et al. |
| 3,800,794 | 4/1974 | Georgi |
| 3,890,968 | 6/1975 | Pierce et al. |
| 4,001,801 | 1/1977 | Moulet |
| 4,038,981 | 8/1977 | LeFevre et al. |
| 4,105,028 | 8/1978 | Sadlier et al. |
| 4,168,707 | 12/1979 | Douvas et al. |
| 4,173,224 | 11/1979 | Marx et al. |
| 4,213,454 | 7/1980 | Shim |
| 4,261,388 | 4/1981 | Shelton |
| 4,321,461 | 3/1982 | Walter, Jr. et al. |
| 4,328,801 | 5/1982 | Marx et al. |

OTHER PUBLICATIONS

Gibbs, "Laboratory Methods, Drop-Recorders", *Journal of Laboratory and Clinical Medicine*, 1926, pp. 686-692.
Gundersen, "Pitfalls in Drip-Infustion Technique", *Acta*, 1972, 16, pp. 117-122.
Zinner et al., "Drop Spectrometer", *The Journal of Urology*, vol 101, Jun. 1969, pp. 914-918.

*Primary Examiner*—Edward M. Coven
*Attorney, Agent, or Firm*—Fleit, Jacobson, Cohn & Price

[57] ABSTRACT

A flow monitor including an optical sensing chamber and an electronic controller which allows determination of exact drop volumes and flow rates. In one embodiment, the flow monitor forms part of a gravity fed volumetric controller in an IV system. In another embodiment, the flow monitor takes the form of a urinary output monitor in a urine collection system. Basically, the flow monitor comprises a microcontroller which responds to parametric information fed into the system through a keyboard and variable information detected by a novel drop diameter detector. The electronic controller, in response to the parametric and variable information being fed into it, is able to determine the precise volume of IV solution or urine passing through the respective systems. In the volumetric controller, the microcontroller causes a linear actuator to control the diameter of a flexible pinch tube found in the IV system. Under one mode of operation, the diameter of the pinch tube is regulated to control drop size. In another mode of operation, the diameter of the tube is regulated to control the time interval between drops. By selectively combining the two modes of operation, a precise volume of IV fluid may be administered to a patient. Also forming part of the system are audible and visual alarms to alert the user to any malfunctions in need of correction.

26 Claims, 26 Drawing Figures

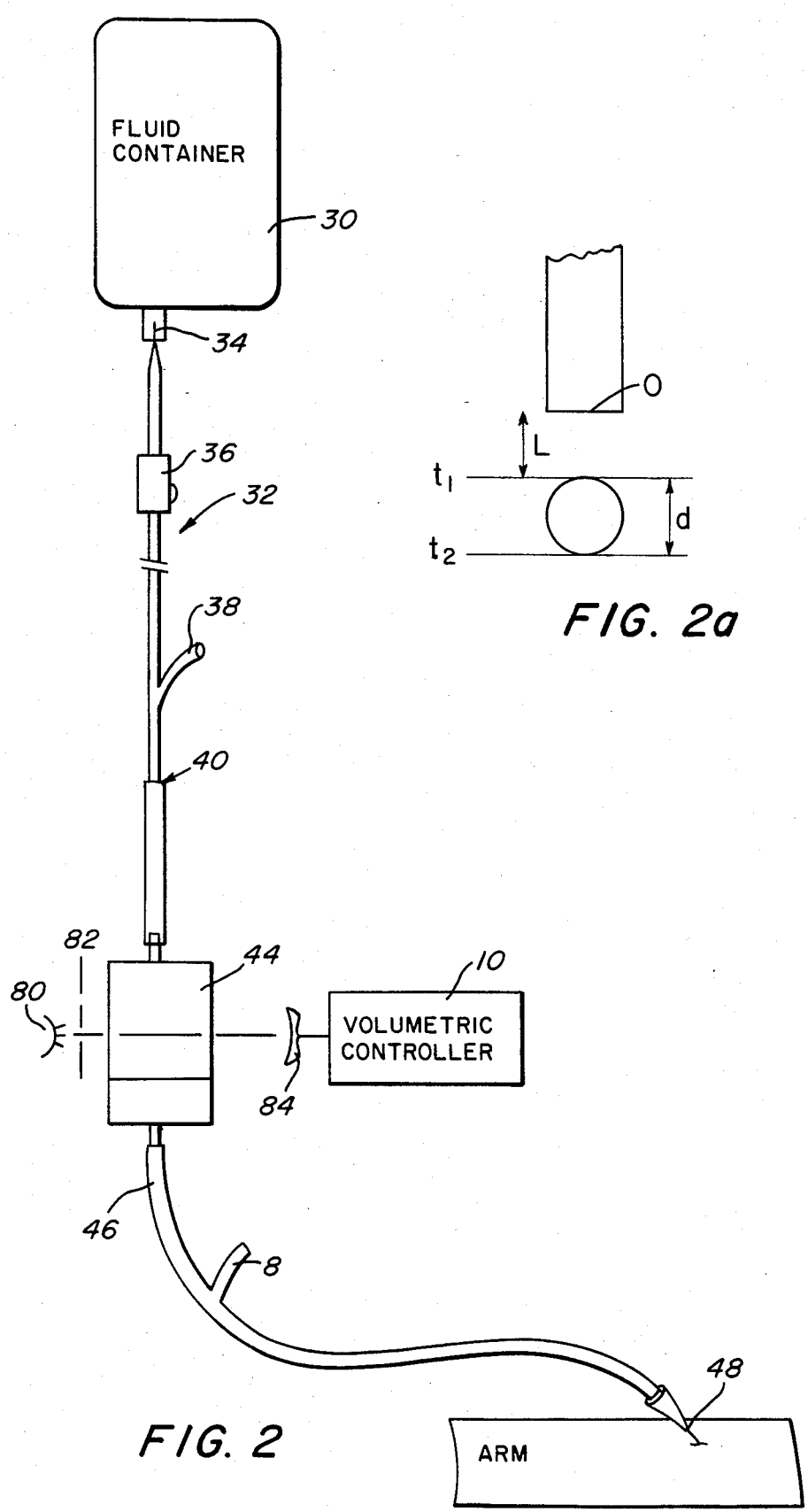

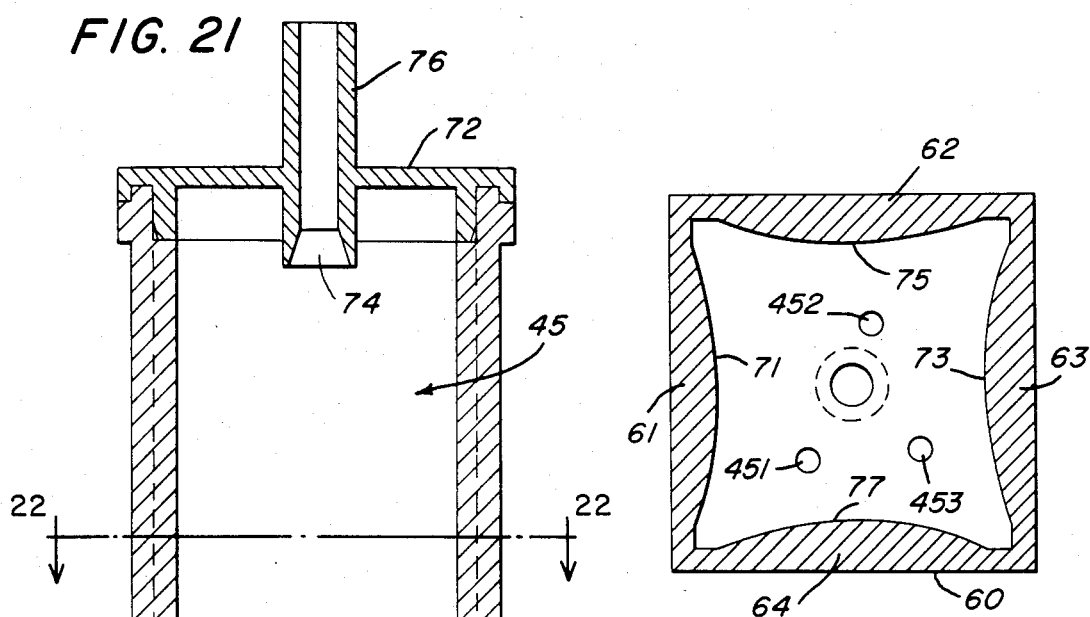
FIG. 21
FIG. 22
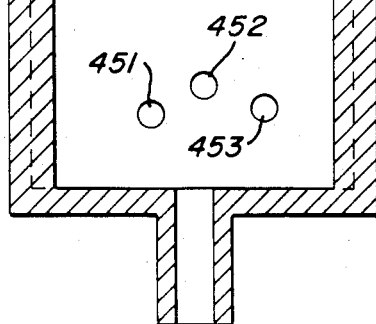
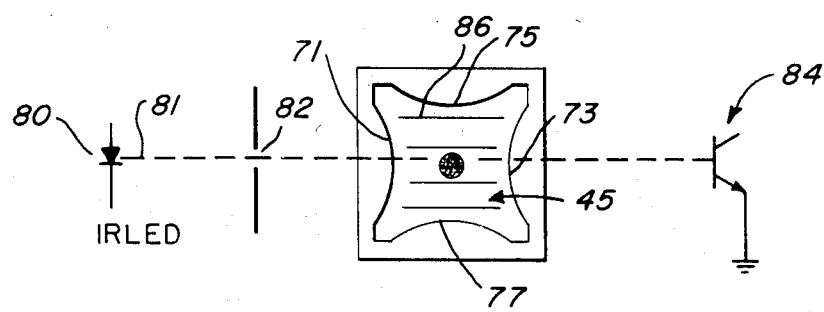
FIG. 3

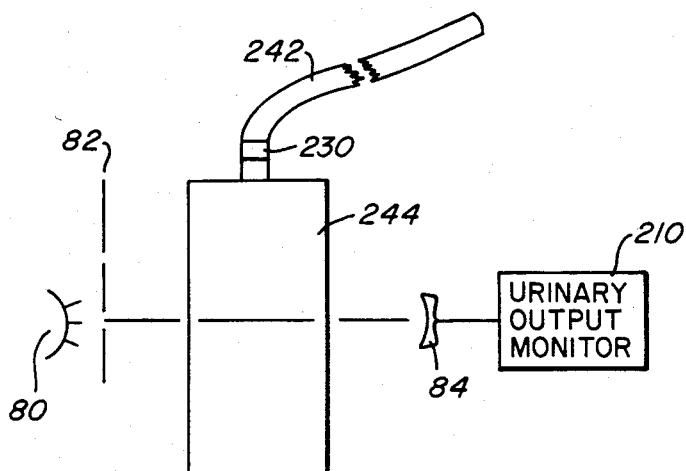
FIG. 19
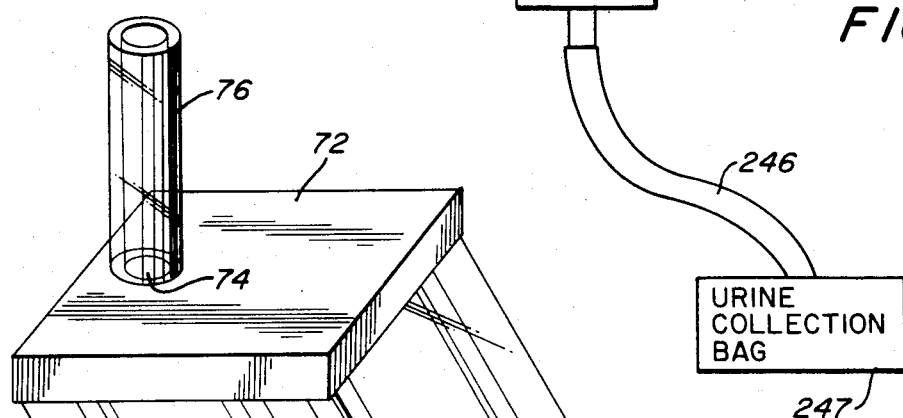
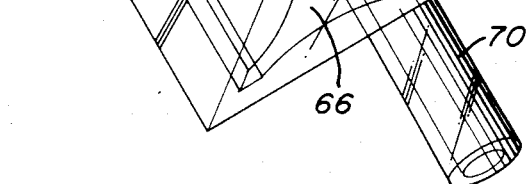
FIG. 20

FLOW RATE MONITOR WITH OPTICAL SENSING CHAMBER

REFERENCE TO RELATED APPLICATION

This is a continuation-in-part of U.S. patent application Ser. No. 452,395, filed Dec. 22, 1982, abandoned.

BACKGROUND OF THE INVENTION

1. Field of the Invention

The present invention relates to flow monitors in general and to a gravity fed volumetric controller and a urinary output monitor, each having an enhanced drop size determination technique including an improved lensing capability necessary to make for simplified drop collection and determination, in particular.

2. Background of the Invention

In the development of fluid flow monitors, the first flow monitors were simply drop recorders, known as drop counters, and now are known as flow rate monitors and controllers. Certain flow rate monitors are used to monitor the production of urine by a patient. Other flow rate monitors are used to monitor and control the introduction of fluids into a patient as by IV infusion. In addition there are mechanical and electronic infusion pumps and controllers used today for parenteral and enteral use.

Basically, there are three categories of devices for IV infusion: gravity IV administration systems, infusion controllers, and infusion pumps.

Gravity IV administration systems utilize a traditional bag or bottle containing a fluid or drug and a flexible administration set. Typically, the flow control of the set is governed by a manual clamp of the screw or roller type. The height of the bottle provides a pressure head that allows the fluid to overcome venous pressure and permits the drug to enter the venous system. However, in recent years, gravity systems have been reviewed for efficacy because of inaccuracies in flow rate.

Infusion controllers, like IV systems, work by gravity and exert no pressure. The controllers count drops electronically and extrude volumes of fluid mechanically and electronically. Because they have relatively few moving parts, infusion controllers are less complex than infusion pumps and are usually less expensive and have fewer maintenance problems.

Infusion controllers may be classified in two groups: volumetric and non-volumetric. In a non-volumetric controller, accuracy is determined by drop rate. The major difference from the traditional IV set is that in a volumetric controller, control of flow is regulated automatically rather than manually.

Infusion pumps differ from the other methods discussed in that they do not depend on gravity to provide the pressure required to infuse the drug. Pressure is provided by an electric pump motor that propels a syringe, a parasystolic or roller device, or a refillable chamber calibrated to deliver a prescribed volume. Most pumps are volumetric and may be adjusted to deliver a drug under different pressures. Among the problems associated with infusion pumps are air embolism occurring despite the use of filters, IV solution bags running dry, clogged catheters, infiltration, extravasation of fluids, phlebitis, and painful IV sites.

Recently, there has been interest in the provision of an accurate gravity type IV administration infusion controller. Two examples are found in U.S. Pat. No. 4,105,028 to Sadlier and U.S. Pat. No. 4,173,224 to Marx. These two patents demonstrate drop size variations due to numerous factors, such as viscosity, rate, etc. These patents suggest two approaches to make their drop recorders and controllers more accurate.

With regard to urinary output monitors, numerous techniques have been devised to monitor urine flow including ultrasonically determining the fluid level and amount of fluid collected, weighing the urine as it is collected in a bag, employing spinning turbines, and other similar techniques.

In intensive care therapy, it is important to accurately monitor the volumetric outflow of urine from a patient in order to facilitate diagnosis of the types of disease states suffered by a patient. Further, it is important to know the urinary output on a volumetrically accurate basis to make clinical judgments, as to the appropriate amount and type of intravenous fluid therapy to be given the patient. Hence, urinary flow rates over varying periods of time become important parameters for the clinician to evaluate.

Thus, there is still a need for a gravity fed IV infusion controller having improved drop size determination techniques and including accurate lensing capabilities to make for a simplified drop collection and determination. Likewise, there is a need for a volumetric urinary output monitor including an optical sensing chamber and an electronic monitor which allows determination of the exact drop volume and flow rates. The present invention is directed toward filling these needs.

SUMMARY OF THE INVENTION

One aspect of the present invention is directed toward a gravity fed volumetric controller including an optical sensing chamber and an electronic controller which allows determination of exact drop volumes and flow rates. Another aspect of the present invention is directed toward a volumetric urinary output monitor also including an optical sensing chamber and electronic circuitry which allows determination of exact drop volumes and flow rates.

Basically, the gravity fed volumetric controller comprises a microcontroller which responds to parametric information fed into the system through a keyboard and variable information detected by a novel drop diameter detector. The electronic controller, in response to the parametric and variable information being fed into it, responds by causing a linear actuator to control the diameter of a flexible silicone pinch tube, one type of silicone being Silastic found in the IV system. Under one mode of operation, the diameter of the pinch tube is regulated to control drop size. In another mode, the diameter of the tube is regulated to control the time interval between drops. By selectively combining the two modes of operation, a precise volume of IV fluid may be administered to a patient.

Also forming part of the system are audio and visual alarms which are indications of infusion, air in the IV line, low battery condition, system malfunctions, and indications of free flow rate and when infusion has been completed.

In the case of the urinary output monitor, the system basically comprises a microcontroller which responds to parametric information fed into the system through a keyboard and variable information detected by the novel drop diameter detector. The urinary output monitor responds to the parametric and variable information being fed into it by measuring the size of the drops of urine formed in the drip detector and using this information to carefully and accurately monitor urinary output.

Thus, it is a primary object of the present invention to provide a flow monitor which allows determination of exact drop volumes and flows rates of IV solutions or urine.

It is another object of the present invention to provide an improved gravity fed volumetric controller.

It is yet an object of the present invention to provide an improved urinary output monitor.

It is a further object of the present invention to provide an improved optical sensing chamber which facilitates the determination of exact drop volumes and flow rates.

It is still further an object of the present invention to provide a universal disposable optical sensing device as a way to provide accurate measurement of drop volume.

BRIEF DESCRIPTION OF THE DRAWINGS

FIG. 2 is a diagrammatic illustration of the volumetric controller in use in a gravity intravenous administration set.

FIG. 2a is a schematic diagram used to explain the calculation of drop volume as the drops pass through the drop sensing chamber.

FIG. 3 is a schematic diagram used in explaining how the presence of a drop in the sensing chamber is detected.

FIG. 19 is a diagrammatic illustration of the urinary output monitor in use in a urine collection system.

FIG. 20 is a perspective view of an alternative sensing chamber for use in the urinary output monitor and embodying the teachings of the subject invention with its cover removed.

FIG. 21 is a longitudinal section of the sensing chamber which is schematically illustrated in FIG. 19.

FIG. 22 is a view taken along lines 22—22 of FIG. 21.

DETAILED DESCRIPTION OF THE PREFERRED EMBODIMENT

Figure 1:
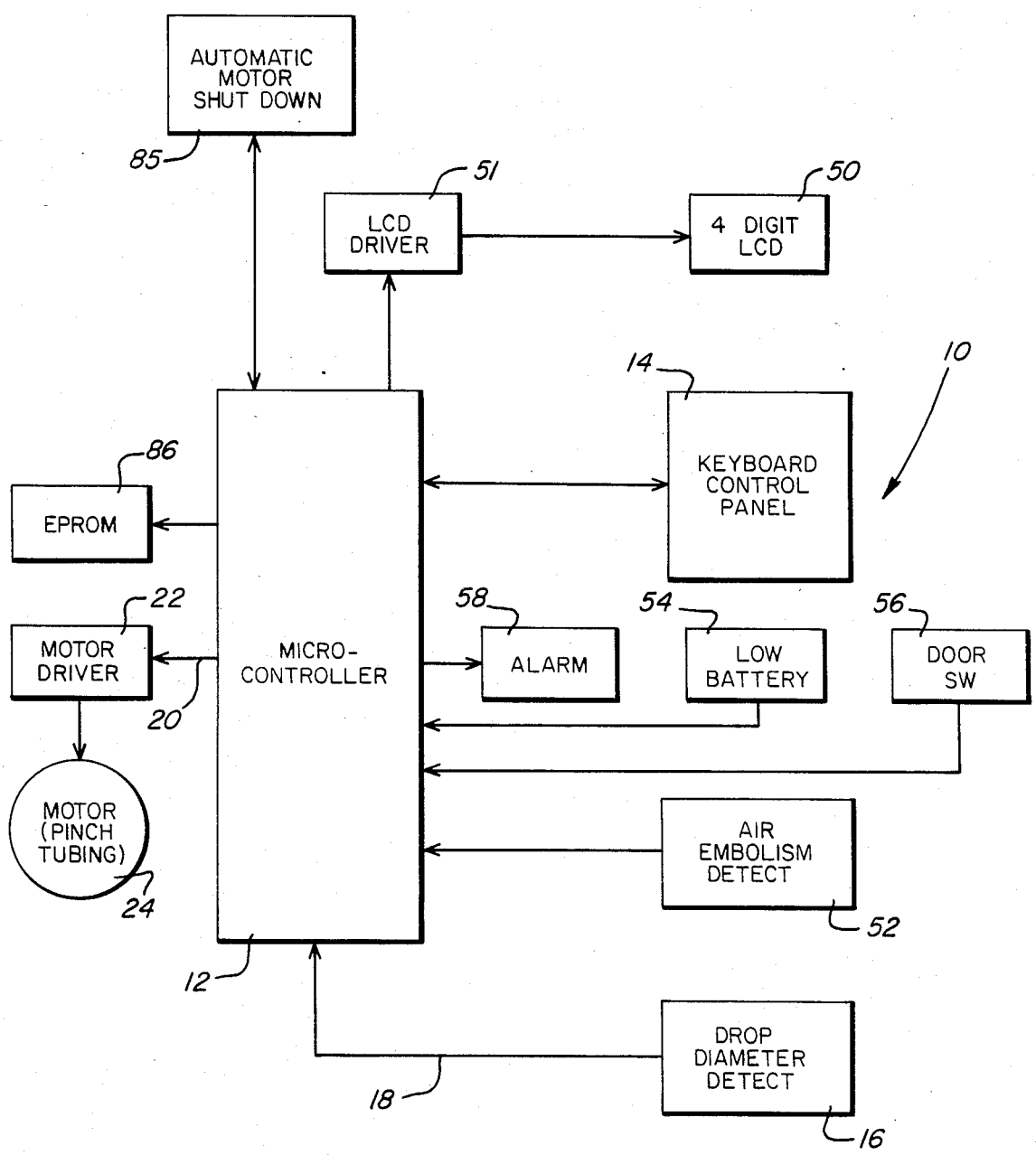
FIG. 1 is a block diagram showing the major components of an embodiment of a volumetric controller employing the teachings of the subject invention.
Figure 9:
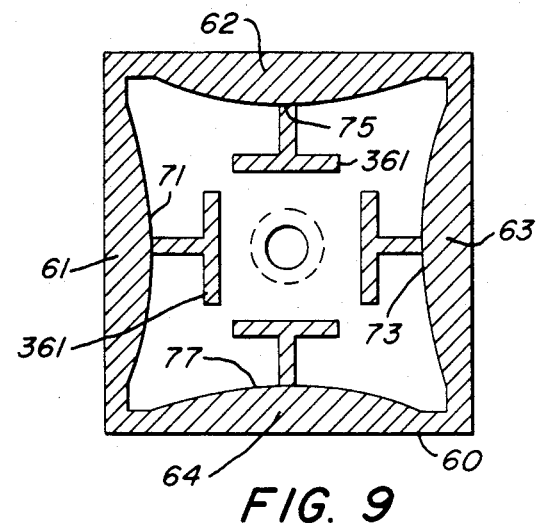
FIG. 9 is a view taken along lines 9—9 of FIG. 8.

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar purpose.

The basic elements constituting the volumetric controller are collectively designated as 10 in FIG. 1. At the heart of the gravity fed volumetric controller is a microcontroller 12. In a preferred embodiment, the micrcontroller is a ROMless microcontroller (such as that carrying product identification No. COP404LS, as manufactured by National Semiconductor) used with an auxiliary EPROM 86. It is to be understood, however, that the ROMless microcontroller and its auxiliary EPROM could be replaced by any conventional microcontroller with internal ROM. A keyboard control panel 14 is provided to place information into the microcontroller 12. The control panel is used to provide certain commands to the microcontroller, such as start, pause, change rate, etc. Certain other information, such as the volume to be infused, is also provided to the microcontroller through the control panel.

Also forming part of the volumetric controller is a novel drop diameter detector 16, which will be described in greater detail hereinafter. Suffice it to say at this point, the detector 16 provides information to the microcontroller on lines 18. The information is in the nature of a signal representative of the presence and, a function of the diameter of fluid drops as they pass through the IV set.

With the information provided by the keyboard 14 and the drop diameter detector 16, the microcontroller 12 produces a signal on lines 20, which in turn causes a motor driver 22 to activate a linear actuator in the form of a stepper motor 24 to alter the diameter of a Silastic tubing in order to alter either the size of the drops passing the drop detector or the duration between drops passing the drop detector.

Circuitry constituting an automatic motor shutdown 85 communicates with the microcontroller 12. The motor shutdown, which will be described in greater detal hereinafter, lets the microcontroller know that the power has been turned off. The microcontroller, in turn, directs power from a battery to, in effect, cause the motor 24 to pinch the Silastic tubing closed.

The volumetric controller is intended to be used as part of a gravity IV administration system. With reference to FIG. 2, a diagrammatic illustration of a gravity IV administration system is presented. Basically, the system comprises a traditional bag or bottle 30 containing a fluid or drug and an administration set 32. A spike 34 is provided to enter the fluid container 30. Positioned downstream from the spike 34 is a clamp, such as a roller clamp 36. Further downstream, there is defined within the PVC tubing an injection site 38. Below the injection site, the PVC tubing terminates at point 40, where it is secured in a conventional manner as by friction or adhesive to a Silastic or other type of flexible tubing 42. The other end of the Silastic tubing is secured in much the same way to the top of a drop volume detecting chamber 44 forming part of the drop diameter detector 16. The bottom of the chamber 44 is secured, again as by friction or adhesive, to a PVC tubing 46, which has its distal end secured to an appropriate needle 48 for injection into the arm of a patient. It is possible to provide an injection site 48 somewhere within the tubing 46. As drops pass through the drop volume chamber 44, their presence and duration are detected by the volumetric controller 10.

In order to enable the user to determine the type of information being entered by the keyboard control panel into the microcontroller, an LCD (liquid crystal display) 50 driven by an appropriate LCD driver 51 under signals generated by the microcontroller is provided. Finally, certain protective features, such as an air embolism detector 52, a low battery detector 54, and a door open detector 56 are provided. Each of these detectors provides information to the microcontroller 12, which in turn activates an alarm 58.

Figure 8:
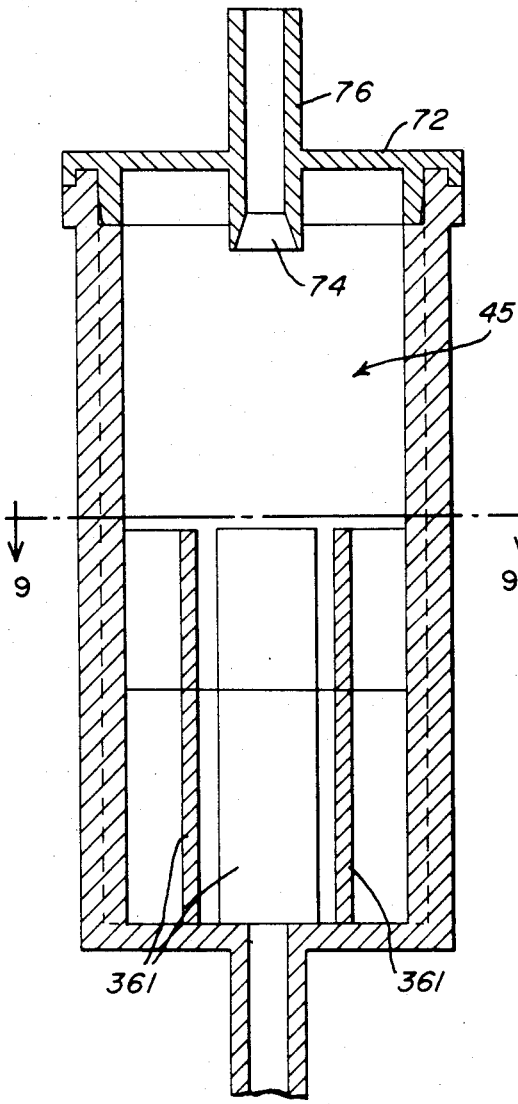
FIG. 8 is a longitudinal section of the sensing chamber of FIG. 4 with the cover in place.
Figure 4:
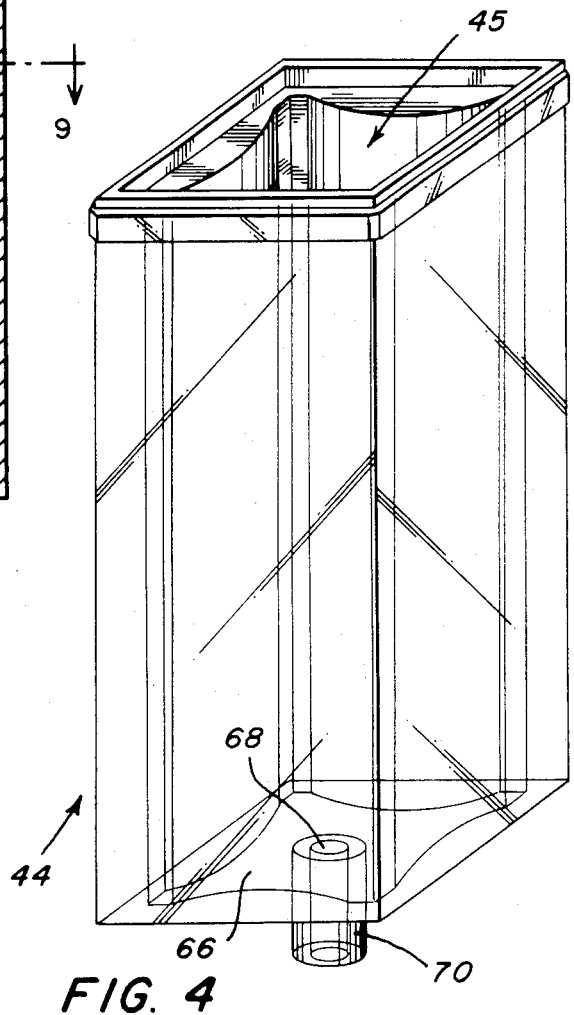
FIG. 4 is a perspective view of a sensing chamber embodying the teachings of the subject invention with its cover removed.

With reference to FIGS. 2-4, 8 and 9, the details of the sensing chamber 44 will now be described. In its position of intended use, as shown in FIGS. 4 and 8, the sensing chamber 44 basically comprises an elongated vertically oriented hollow housing. When viewed in transverse cross section (FIG. 9), the exterior surface 60 of the housing has the general configuration of a square. Defining a portion of the interior cavity of the chamber 44 are four vertically oriented walls 61 through 64. Each of the walls has associated with it the periphery of one of the sides of the square cross section. As constructed, walls 61 and 63 are oriented generally parallel to each other as are walls 62 and 64. The interior surfaces of each wall are generally curved to define one of the four lenses 71, 73, 75 and 77. Of particular importance is that the lenses be molded so that they are consistent in size, and also so that they repeatedly produce a focal length of approximately 2 inches.

Four splash walls 361 are placed in the interior of the chamber to perform two major functions: (1) minimize droplets forming on the lensing surfaces and (2) decrease the interior volume of space, hence: reducing the potential dump volume and reducing the time to occlusion interval. The four splash walls are parallel to the lenses and perpendicular to the bottom of the chamber.

The bottom 66 of the chamber 44 contains a centrally located aperture 88. Emanating downwardly from the aperture is a hollow projection 70. The projection 70 is secured to one end of the PVC tubing 46 to provide fluid communication between that tube and the interior of the cavity. At the top portion of the chamber 44, there is provided a cover plate or cap 72. The interior of the cap defines the final surface constituting the interior volume 45 of the chamber 44. Centrally located on the cap is an aperture 74. Protruding upwardly from the aperture is a hollow projection 76. This projection is connected to one end of Silastic tubing 42 to create a fluid communication between the interior of the sensing chamber 44 and the Silastic tubing.

Figure 5:
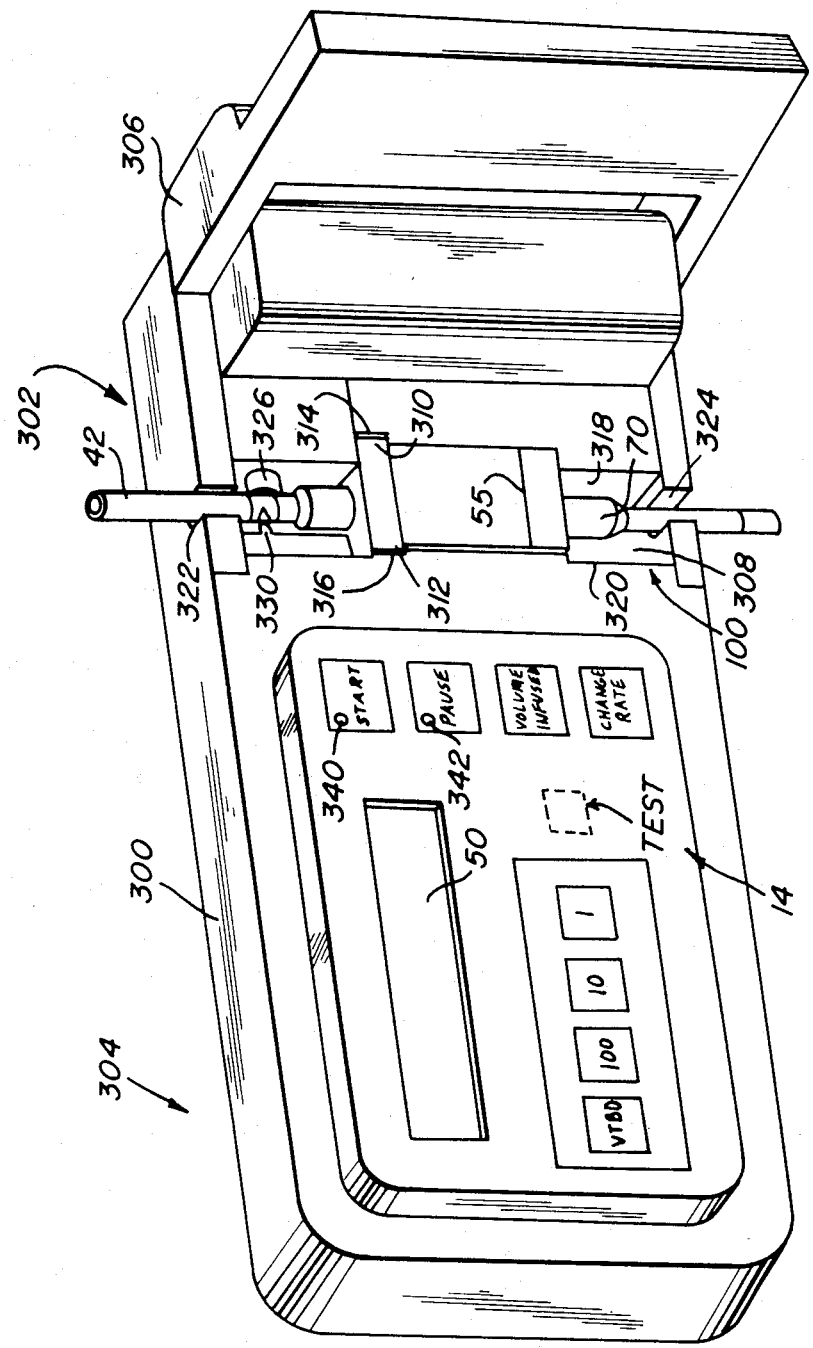
FIG. 5 is a perspective view of the front of an instrument forming part of the volumetric controller.
Figure 6A:
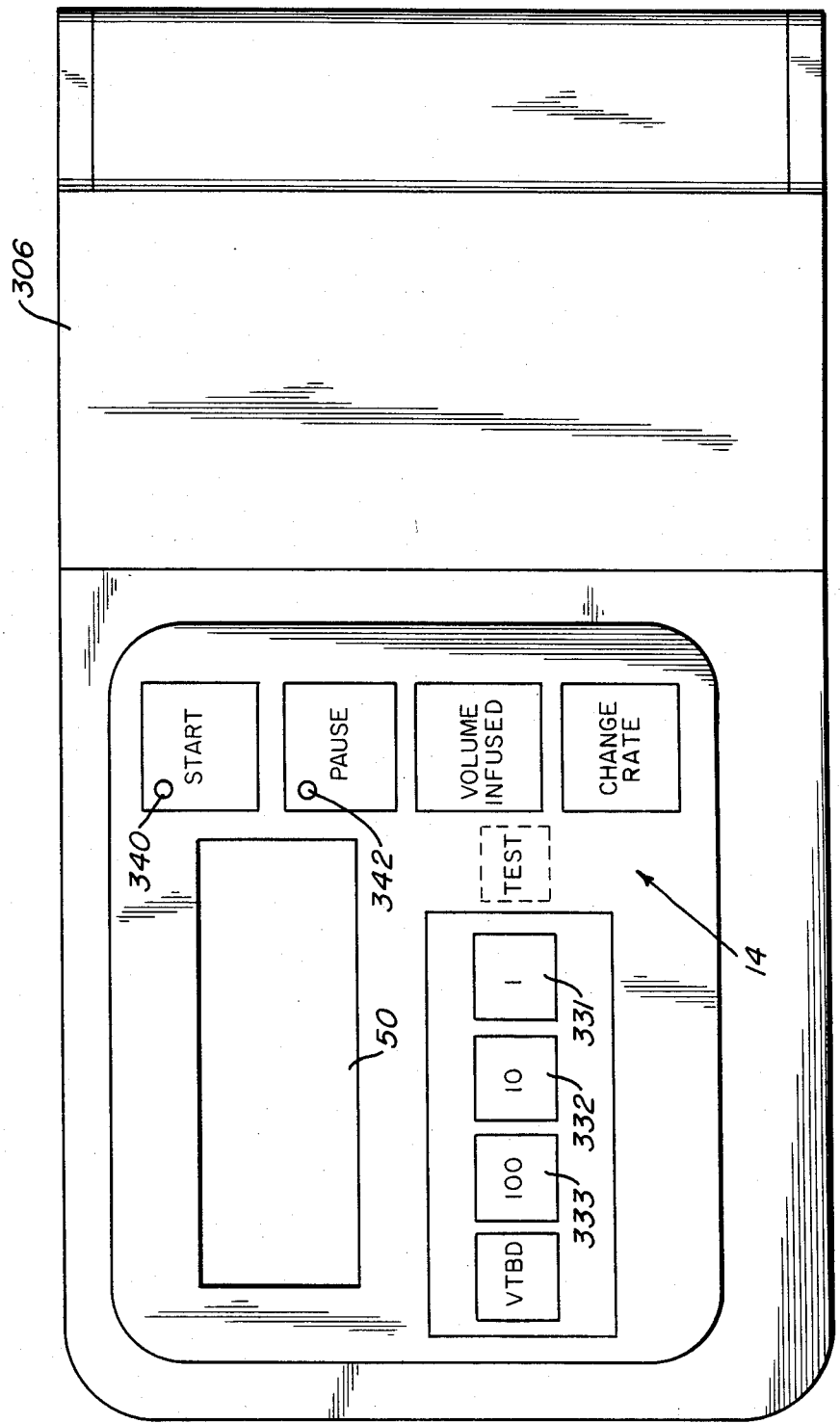
FIG. 6a is a front plan view of the instrument of FIG. 5 with the door closed.
Figure 6B:
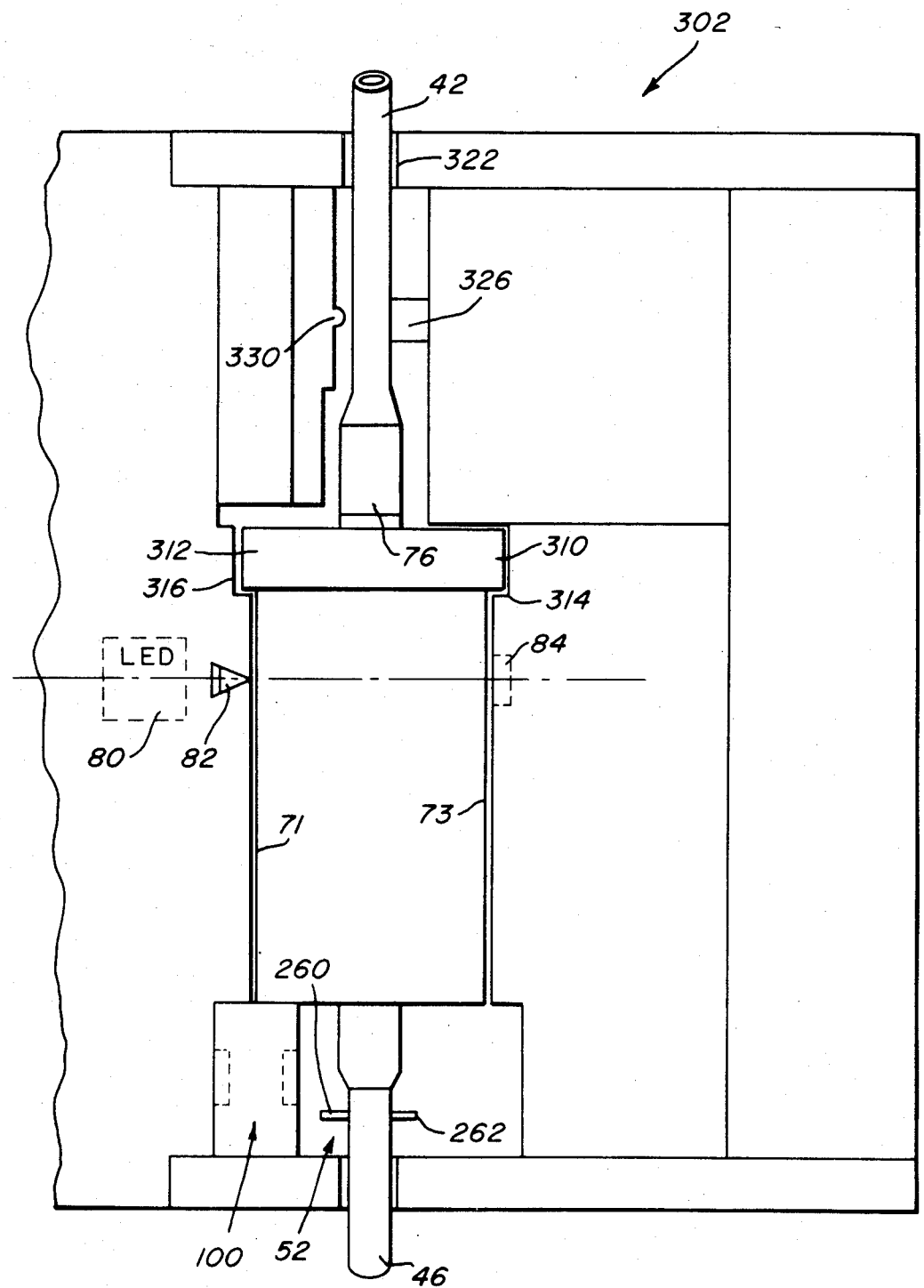
FIG. 6b is a front view of the sensing chamber receiving portion with a sensing chamber mounted therein.

With reference to FIGS. 5, 6a, and 6b the details of the structure which houses the volumetric controller will now be described.

A housing 300 is generally divided into two portions. As oriented in FIG. 5, the right-hand side 302 of the housing provides a general area for receiving the drop volume chamber 44. The left-hand side 304 of the housing defines a portion for receiving the electronics associates with the operation of the volumetric controller and also provides the control panel with the keyboard 14 and the display 50.

A door 306 is hingedly mounted and is free to swing back and forth so that in its open position it reveals the cavity 308 within which the drop volume chamber 44 is mounted. In its closed position, the door 306 covers the cavity 308 to secure the drop volume chamber 44 within the cavity 308.

The cavity 308 is configured to accommodate the drop volume chamber 44 in one orientation. This is accomplished by providing keys 310 and 312 at the upper portion of the drop volume chamber 44. These keys mate respectively with keyways 314 and 316 provided in the sidewalls 318 and 320 of the cavity 308. Channels 322 and 324 are provided at the top and bottom of the chamber 308 to permit insertion of the administration set associated with the IV system. Defined at the top of the cavity 308 is the plunger 326 of the actuator motor 24. The plunger moves to the left or right as illustrated in FIGS. 5 and 6b. When moved to the left, the plunger urges the Silastic tubing 42 up against the anvil 330 to provide a convenient means to control constriction of the tube 42.

The back side (not shown) of the body 300 contains a conventional clamp for securing the volumetric controller housing to a conventional IV stand.

In use, the sensing chamber 44 is positioned as oriented in FIGS. 5 and 6b within the volumetric controller. When positioned within the volumetric controller and in use, an infrared LED (light emitting diode) 80 passes a beam of light through a slit 82. The beam of light is then passed through lens 71 and onto lens 73 for reception by a phototransistor 84. As can be seen with reference to FIGS. 3 and 6b, the lenses are positioned so that they create a series of parallel light rays 86 within the chamber cavity 45.

Having described the details of the sensing chamber, the details of the remaining elements of the volumetric controller will now be provided.

At the heart of the volumetric controller 10 is the microcontroller 12. In a preferred embodiment, the microcontroller comprises a ROMless microcontroller bearing product designation No. COP404LS as manufactured by National Semiconductor. In order for the user to interface with the microcontroller, a keyboard 14 is provided. The nine keys of the keyboard are connected in a conventional manner in two sets of three lines each. The first set of lines 81 is connected to three bidirectional I/O (input/output) ports provided in the microcontroller. The second set of three lines 83 is connected to an additional three bidirectional I/O ports provided in the microcontroller. Through the keyboard, the microcontroller can be given certain commands such as start, pause, and change rate. In addition, the volume to be delivered may be established. Finally, the volume infused may be monitored by depressing an appropriate key. Finally, there is provided a test key for testing and calibration during manufacture. A clock provides a frequency of about 2.09 KHz to run the system oscillator of the microcontroller 12.

Forming part of the volumetric controller is a memory 86. In a preferred embodiment, the memory is in the form of an erasable programmable memory such as that bearing product designation No. NMC27C32 as manufactured by National Semiconductor. It is to be understood that such memory and the ROMless microcontroller may be replaced by a known microcontroller with internal ROM. The memory is a 4K UV eraseable and electrically reprogrammable EPROM. The memory is enabled by a signal received from the microcontroller on line 88.

Eight bidirectitonal ROM address and data ports are provided in the microcontroller to transfer address information and receive data information on lines 90. The address information passes through an 8-bit latch 92 and then into the EPROM via lines 94. The data, on the other hand, is received from the EPROM on lines 96, which merge with lines 90. The microcontroller contains additional ROM address outputs which provide address information to the memory on lines 98.

A door sensor 100 consisting of a light emitting diode which impinges upon a phototransistor is positioned generally in the lower left-hand corner of the receptacle 308. The door sensor 100 is used to provide a signal on line 102 to the microcontroller through a general purpose input 104. A high signal on line 102 indicates that the door of the volumetric controller is shut.

Another line 106 is connected to a general purpose input 108 of the microcontroller. Lines 102 and 106 are connected to each other via a diode D1 which has its anode connected to line 102. Line 106, in turn, is connected to the cathode of diode D2 which has its anode connected to the anode of diode D3. The cathode of diode D3 is connected to a further general purpose input 110 via line 112.

The junction of the anodes of diodes D2 and D3 are connected to the center pole 114 of on/off switch 116 and the cathode of diode D4. The anode of diode D4 is, in turn, connected to an input of a voltage regulator 118. In a preferred embodiment, the voltage regulator is a three terminal regulator with 5-volt range and is generally designated as LM78LO5 ACZ by National Semiconductor. The output and common ports of the voltage regulator are connected to capacitor C4, whereas the common and the input of the voltage regulator are connected to capacitor C3 and ground. The voltage regulator 118 is used to provide a regulated voltage supply, which in the preferred embodiment is 5 volts.

The microcontroller contains a general purpose output 120 which is connected to the gate of MOS FET-1 (metal oxide semiconductor field effect transistor). The drain of FET-1, in turn, is connected to the gate of FET-2. The source of FET-1 is connected to ground, whereas the source of FET-2 is connected to the gate of FET-1 via resistor R2. The drain of FET-1 is connected to the input of the voltage regulator. With regard to the double throw switch 116, the lower contact of the switch is connected to ground, whereas the upper contact 130 is connected to the source of FET-2.

When the switch 116 is turned from on to off, the diodes D2 and D3 conduct to the interrupt lines 108 and 110. By so doing, the microcontroller 12 knows that the power has just been turned off. The microcontroller then instructs line 120 to turn on and to direct the supply from battery 117 to the voltage regulator 118 via diode D4 for an additional one half of a second. The regulated voltage from regulator 118 powers the motor 24 that is instructed to close down the Silastic tubing 42 in order to stop IV flow through the IV system. Once that one-half second passes, the system turns off. In similar fashion, when the door 306 is open, line 104 is low. That causes diode D1 to conduct which, in turn, causes lines 104 and 108 to both be low. In this way, the microcontroller knows that the door is open and not that the power has been turned down. By connecting diodes D2 and D3 anode to anode, the microcontroller can discriminate between "door open" and "power down".

The microcontroller 12 contains a bidirectional I/O port 140 and a general purpose output 142 which are connected to a Schmitt trigger 144, the output of which is connected to the gate of FET-3. The source of FET-3 is connected to ground, whereas the drain of FET-1 is connected to the input of a shift register 146. In a preferred embodiment, the shift register is an 8-bit parallel-out serial shift register, such as that bearing product designation No. MM74C164 and manufactured by National Semiconductor. The shift register, in turn, produces a first output signal on line 148, which is directed to the linear actuator 24. The shift register produces appropriate output signals on lines 150 and 152 to operate a green and red light emitting diode, respectively. Finally, the shift register produces a signal on line 154 to activate the alarm 58.

A further bidirectional I/O port 60 of the microcontroller and a general purpose output 162 are coupled with general purpose output 142 into the LCD driver 51 which, in turn, produces appropriate signals on lines 166 to activate the LCD display 50.

Also forming part of the volumetric controller is an A-to-D (analog-to-digital) converter 170. One such converter which has been used in a preferred embodiment bears product designation No. ADC0834 and is manufactured by National Semiconductor. The A-to-D converter 170 is activated by signals provided on serial input and bidirectional I/O port on lines 172, on serial clock line 174, and on chip enable line 176. The A-to-D converter contains four inputs 178 through 181 for receiving analog data. Input 178 receives analog signals from bubble sensor 52 which is activated by the microcontroller by a signal generated from a general purpose output 182. The bubble sensor 52 generally comprises an LED light source 260 in combination with a phototransistor 262. The bubble sensor is located in chamber 308 so as to monitor the flow of IV solution through the lower tubing 46. Input 179 receives a signal from the drop sensor 16 which is activated by the microcontroller via signals generated on general purpose output 184. Input 180 receives a low battery reference signal from block 54. Finally, input 181 receives an ambient light signal from ambient light detector 55 which may be positioned anywhere on the outside of the housing 300, for example, at the upper left-hand corner next to display 50.

The final building block of the volumetric controller is the floating trigger, generally designated as 410. The floating trigger basically comprises a group of resistors, capacitors, and operational amplifiers. In particular, the output of the phototransistor 84 of drop diameter detector 16 is fed to the negative input of operational amplifier (op amp) 202 via resistor R6 and capacitor C6 connected in series. The output of operational amplifier 202 is fed back to the negative input of amp 202 by the parrallel arrangement of resistor R8 and capacitor C8 and also to the positive input of op amp 206. The output of op amp 206 is fed to bidirectional I/O port 212 of the microcontroller. The output of the drop diameter detector is also fed to the positive input of op amp 204 via resistors R10 and R16 arranged in series. A capacitor C10 is arranged in parallel with resistor R16.

The output of op amp 200 is fed to the positive input of op amp 204 and also fed back to the negative input of op amp 200. The positive input of op amp 200 is connected to ground via a parallel arrangement of resistor R22 and capacitor C12. The output of op amp 204 is fed to ground through a pair of resistors R18 and R20 in series. At the series junction, the resistors are connected to the negative input of op amp 206. The output of op amp 204 is also fed to the positive input of op amp 202. The negative input of op amp 204 is connected to the positive input of op amp 202 via resistor R14.

The idea behind the floating trigger is to provide a signal indicative of drop size or drop duration that is independent of changes in the VCE of the phototransistor 84. A common phenomenon of light emitting diodes and phototransistors is electronic drift which, in turn, causes the collector-emitter voltage or VCE to drift also. Such VCE drift could jeopardize the accuracy of the duration measurement of the drop. Additionally, in the electronc circuitry found in the volumetric controller, power supply drift may occur. With power supply drift, the LED and phototransistor, again, drift to adversely affect the VCE of the phototransistor 84. Finally, if there is fluid or drops on the sidewalls or lenses of the disposable drop chamber 44, a change in VCE will occur.

The output of the phototransistor 84 of the drop diameter detector 16 is fed into the negative input of operational amplifier (op amp) 202 via resistor R6 and capacitor C6. Also, a bias voltage of about +2.0 volts is supplied to the positive input of op amp 200 via resistor R23. The output of op amp 200 is about 2.0 volts and is applied as a bias voltage to the parallel arrangement of capacitor C10 and resistor R16 and into the positive input of op amp 204. The resulting DC voltage is divided between resistors R10 and R16 and appears at the positive input of op amp 202. The information containing the drop duration from drop sensor 16 is AC coupled through resistor R6 and capacitor C6 into the negative input of op amp 202 by the time a trigger voltage level is set through resistors R18 and R20. That trigger voltage, which goes into the negative input of op amp 206, floats so that the pick off point on the AC signal moves up and down in an inverse direction so as to compensate for changes in the VCE of phototransistor 84. In this way, the drop duration is independent of the electronic drift, in general, and VCE drift, in particular.

Having described the details of the elements constituting the volumetric controller, the way in which a preferred embodiment of the volumetric controller produces an accurate measurement of the volume of fluid passing through the IV system is as follows. With regard to FIGS. 3, 6b and 7, the light source 80 produces a beam 81 which passes through a slit 82 and through the lens of the drop sensing chamber 44. The lenses 71 and 73 are configured to produce parallel rays 86 within the housing. The light from the LED, after passing through the lenses and slit, is received by a phototransistor 84. The output of the phototransistor is operative with the floating trigger to provide the input signal to the microcontroller. Thus, the light source 80 and the phototransistor 84 with the slit aperture 82 define a plane of light through which the drop passes. As the drop breaks the plane of light, the phototransistor output appears as a rising analog signal as the drop enters the parallel rays of light. The output of the phototransistor remains constant while the drop is contained within the parallel rays of light and gradually drops as the drop leaves the parallel rays of light. This signal is fed into the floating trigger 210 which produces a square wave with a duration in milliseconds proportional to the diameter of the drop. In particular, the output of the floating trigger is high in the absence of a drop and is low as the drop passes through the boundaries defined by the parallel rays of light.

With reference to FIG. 2a, t1 represents the time it takes for a drop to reach a distance L from the orifice O. Time t2 represents the time it takes for that drop to travel a distance equal to its diameter d. Thus, using the known free falling equation and the gravitational constant "a", t1 is equal to $$\sqrt{\frac{2}{a} L} ,$$

whereas t2 equals $$\sqrt{\frac{2}{a} (L + d)} .$$

t2−t1=T which equals $$\sqrt{\frac{2}{a}} (\sqrt{L+d} - \sqrt{L}) .$$

If L is chosen small when compared to d, then T approximately equals $$\sqrt{\frac{2}{a}} d^{\frac{1}{2}}$$

or $T^2=KD$.

Since drop volume can be controlled over a short range of values and since $V=(4/3)\pi r^3$ or $(\pi d^3/6)$, then over a narrow range of drop volumes, the linear approximation of V is $KT^2$.

The square wave signal generated at the output of the floating trigger is approximately 20 milliseconds in duration and is fed to the microcontroller which is able to solve the equation for volume equals $KT^2$. The microcontroller, by knowing the precise volume, is able to produce a signal on the shift register 146 which causes the linear actuator 24 to move in and out to either constrict or open the Silastic tubing 40 and, thus, either permit or close off the entry of drops into the drop volume chamber 44. In this embodiment, the microcontroller 12 adjusts the time interval between individual drops to thereby maintain an extremely accurate volumetric flow rate. By actually measuring the drop size, it becomes a simple matter to change the linear actuator opening interval and thereby maintain the desired flow rate.

In use, the linear actuator motor 24 and driver 22 function under two parameters controlled by the microcontroller. Initially, the microcontroller issues a signal to cause the linear actuator to completely constrict the Silastic tubing. The microcontroller then issues a signal to cause the linear actuator to move out in small steps of predetermined duration until a drop is detected by the drop diameter detector 16. The number of steps taken in order to detect the first drop is placed into memory within the microcontroller and is used as a reference for each succeeding drop. Thus, the determination of the time interval between drops is based on two factors: the set rate desired by the user and the volume of each drop actually measured in terms of time in milliseconds.

In another mode of operation of the subject invention, the size of the drops is altered rather than the time interval between drops. The microcontroller 12 causes the linear actuator 24 to completely constrict the Silastic tubing 42. The microcontroller then issues a signal to cause the linear actuator to step back. The microcontroller then looks to see if the drop sensor 16 has detected a drop. If not, the linear actuator is instructed to move one additional step back. This continues until a drop is sensed by the drop sensor 16. At this point, the microcontroller determines the volume of drops sensed and then causes the linear actuator to move three steps to stop flow. After a predetermined time interval which remains constant throughout the particular operation, the microcontroller causes the linear actuator to move three steps outwardly until a drop is detected. The volume of that drop is measured and, if it is greater than that desired, then the linear actuator is caused to step down further and then open up less so that the cross section of the Silastic tubing 40 is smaller which results in the next drop being of smaller volume. Thus, the interval between drops is held constant, and the volume of each drop is measured and used to adjust the tubing constriction size. Should the drop be smaller than that predicted by the equation, the motor position is adjusted to increase the volume of the next drop. Similarly, the measurement of oversized drop volumes initiates motor adjustments to decrease subsequent drop sizes. Therefore, the flow rate can be accurately maintained.

Before the very first drop is let through the drop volume chamber 44, the motor 24 closes down on the Silastic tubing 42 as much as possible. It then, at preset intervals, pulls back one step (approximately 0.002 inches) at a time, waiting for the tube to open enough to allow fluid to flow through and, hence, a drop to form and fall. Once the first drop is detected, the motor has found its motor relative position (MRP) and it can completely stop fluid flow by moving in only two or three steps (whereas finding the first drop requires up to 59 steps out from the full shut off position).

From this point, the motor pulls back at preset intervals to allow drops to fall. Motor compensation, therefore, adjusts "effective orifice size" thereby maintaining a uniform drop volume. This coupled with a constant drop frequency provides constant flow control. In this way, the volumetric controller is able to employ the benefit derived from gravity-fed pressures.

In order to dispense precise volumes of IV solution, two major things happen simultaneously in the volumetric controller 10. If there is a slight change in the drop size (say, 0.082 to 0.086 cc), then the microcontroller 12 increases the time interval of when the next drop should occur and then, in fact, opens the motor 24 at that time. Therefore, with an increase in volume a corrresponding increase in time interval occurs thereby maintaining a constant rate of IV solution infusion into a patient.

However, more significantly than simply changing the time interval, the volumetric controller, under certain predetermined conditions, changes the drop size (volume) in order to provide for a constant rate of infusion. The mechanism for changing the drop size, and thereby the drop volume, is done by modifying the effective size of the internal orifice of the pinch tube 42. It has been determined that various fluid types, viscosities, temperature, stepper motor action, adherence of drops to the drop forming orifice and formation of satellite (trailing) drops or extra drops can change the drop size drastically up to 50% or more. If an extra drop of IV fluid comes through the drip chamber 44 at the wrong or unexpected time (due to a quick change in head height, etc.) then the Motor Relative Position (MRP) is changed by moving the stepper motor 24 in one position (i.e., making the effective orifice diameter smaller). If a trailng (satellite) drop is too big, i.e., greater than 10% of a normal drop, then the MRP is altered by one position in the same manner just described.

In addition to compensation for errant drops, the controller also adjusts drop rate and drop size when normally formed drops are either too large or too small; i.e., the drops are outside of the 10% window. If the main drop being observed is larger than a 0.099 cc drop, then the MRP is pushed in one position. If the main drop is smaller than a 0.060 cc drop, then the MRP is pulled out one position, hence, opening the effective internal orifice of the tube 42. Even within the range 0.060 to 0.099 cc/drop, if a main drop is greater or less than approximately 10% of the last normal main drop, then the MRP is pushed in or pulled out one position. If a "squirt" occurs (two or more main drops adhering to one another in a non-spherical form) the floating trigger 210 and the 0.060–0.090 cc/drop limits cause the MRP to be pushed in one step.

Under control signals from the microcontroller 12, the linear actuator or stepper motor 24 operates in the following manner to effectively control drop volume and flow rates through the IV system. During initial activation of the volumetric controller, the plunger 326 of the motor 24 is pushed into the tubing 42 and anvil 330 as hard and far and tight as possible, therefore, no fluid flows at all, and the tube is completely cut off. The start button is pushed and the motor steps out one step at a time until the first drop is seen by the drop diameter detector 16. The motor is immediately pushed in three steps and that location of the motor is called the Motor Relative Position (MRP) and is assigned an arbitrary value of 8.

The volumetric controller now continues in the normal mode of operation. Based on the value of the last drop volume sensed and measured and taking into account the other factors listed above for abberrant drops the following occurs: (1) the next time interval is calculated by the microcontroller; (2) the motor is at MRP equals 8 which represents the number of steps from complete closure to barely pinch off the tube; and (3) when the time interval is over, the motor 24 steps out three steps (one step at a time looking for the drop every 10 ms), if and when the drop is seen by the drop diameter detector then the stepper motor is pushed back in three steps.

If the drop was detected by the drop detector 16 at the predetermined time, then after the motor has moved three steps out, the motor will move three steps in so that the MRP stays at 8. However, if the head pressure were changed slightly and the drop does not come through the chamber 44 during the three motor pull outs, then the motor 24 pulls out another step and the drop detector looks for the drop. Then immediately the motor steps in three steps but this will change the MRP to 9 (i.e., the effective orifice of tube 42 has opened up one step or approximately 0.002").

The converse is also true, suppose the MRP is set at 8. The predetermined time interval has expired and the motor has been pulled out one step (the first of three steps)—no drop is seen and the motor is pulled out one more step (the second of three steps)—a drop is seen. Immediately the motor is pushed in three steps. As a result of this, the new MRP equals 7, i.e., the effective internal orifice has been closed and a new MRP has been established. As stated before, MRP is the position at which the tubing is barely closed off. From that position the tubing is opened with each step and the controller waits to see if the drop is seen by the drop detector. Other conditions also can occur which are taken into account by the volumetric controller. Suppose that MRP equals 8, but the IV site is clotted and no flow can occur. Then, when the time interval expires (a drop is supported to come but cannot because of the clotted IV site) the motor 24 steps out the first three steps and no drop is detected by the drop detector. The motor then continues stepping out, one step at a time, the controller looks for the drop, the motor steps again, the cycle being repeated again and again until when the motor has stepped out a total of eight steps at which point it "falls off a register" and produces a "rate variation" and immediately pushes the motor in all the way as in the initial or pause condition.

To summarize, the volumetric controller 10 normally operates in the following manner. When a predetermined time interval has expired, the pinch motor 24 is pulled-out step by step (typically a total of three steps) until a drop is formed. As soon as the drop crosses the light detector plane 86 in the drip chamber 44, the volumetric controller begins to measure volume. After the volume of the drop has been measured, the controller then determines whether drop volume is within a plus or minus 10 percent window established by the controller. Regardless of whether or not the drop volume is within the prescribed window, the motor then pushes in one step. The controller then determines whether the drop passing the drop detector was part of a squirt. After this, the motor then pushes in two more steps. At this point, the controller determines if the motor relative position (MRP) should be changed based on the drop volume. If so, the motor relative position is then changed. The controller then calculates the time interval when the next drop should be produced.

The motor pinch-off of the volumetric controller is located above the drop former 76 to pinch off the tube above the drop former as opposed to being located to operate on the fluid conduit 46 which extends from the bottom of the drop chamber to the injection site 48 at the patient. In the volumetric controller, the purpose is to control drop size and maintain a given volumetric rate. To this end, in the controller device, before the plunger-anvil alters the opening in the tube 42 leading into the drip chamber 214, a measurement of drop volume is taken. Based on the measured drop volume, the tube leading into the drip chamber is acted on by the plunger-anvil in order to control the size of the drop ultimately produced in the drip chamber.

In the volumetric controller the tube 42 is never pinched off completely, but is closed only to such an extent that internal friction within the tube prevents the formation of additional drops at the drop former within the drip chamber. With reference to FIGS. 2 and 5, only the tube 42 connecting the volume detecting chamber 44 and the traditional IV bag or bottle 30 is pinched or acted on by motor 24 and anvil 330 and the tube 46 which leads from the drip chamber 44 to the IV needle 48 is never altered in any manner.

Figure 7:
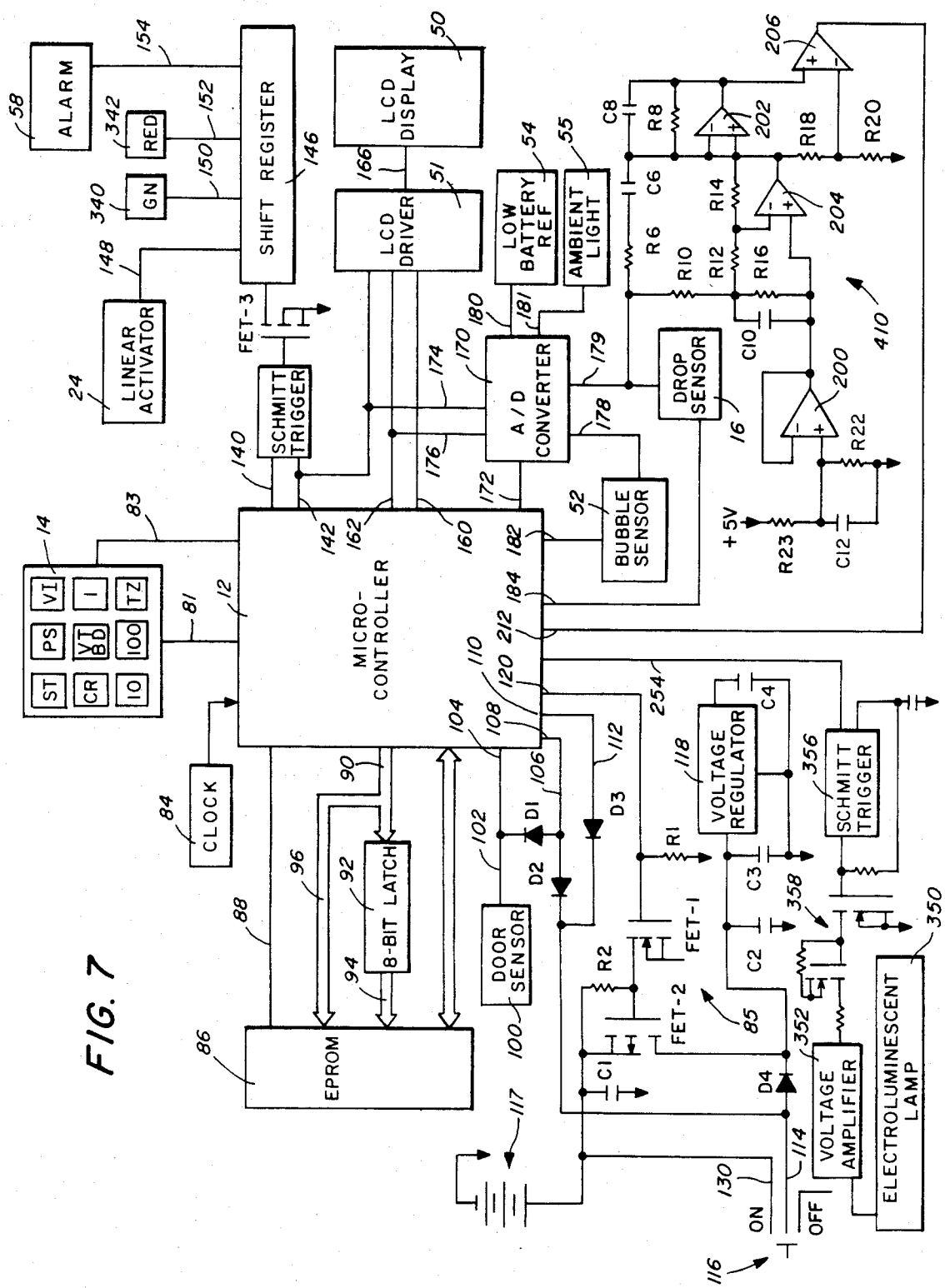
FIG. 7 is a schematic diagram showing the components of the electronic circuitry associated with the volumetric controller.

With reference to FIGS. 2, 5, and 7, the procedure for operation of a preferred embodiment will now be described.

In a situation where a hospital is employing its own IV set, it is recommended that a macro (approximately 15 drops per milliliter) nonvented administration set be used. With reference to FIG. 2, the system is initially set up by closing the roller clamp 36 on the administration set. The IV tubing 46 should then be spiked to the distal end of the drop volume sensing chamber 44. The other end of the sensing chamber 44 should then be spiked into the IV solution container 30. The IV solution container is then suspended in a traditional manner and air is purged from the administration set.

Figure 10:
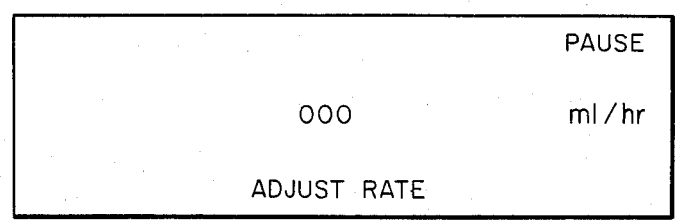
FIGS. 10 through 16 show the various stages of the visual display at various times during the operation of the volumetric controller.
Figure 11:
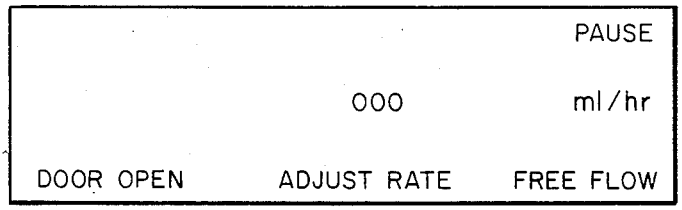

The sensing chamber 44 is tilted and the roller clamp 36 is opened to fill to the fill line 55 shown on the sensing chamber. If the administration set contains a drip chamber, this should be inverted and filled completely to prevent erroneous air and line alarms. The roller clamp should then be closed on the IV tubing 32. The administration set should then be connected to the infusion device with the drop rate adjusted with the roller clamp. Switch 116 is then placed into the ON position. The display 50 will then read as shown in FIG. 10. The door 306 of the unit is then opened. In this situation, the display will read as shown in FIG. 11.

Figure 12:
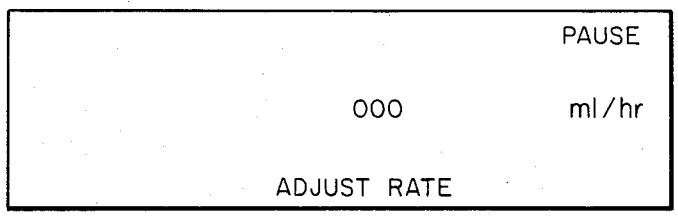

With the door open, the sensing chamber 44 is placed into the receptacle 308. Next, the Silastic tubing 42 is positioned within the channel 322 above the sensing chamber. The door is then closed. With the door closed, the volumetric controller will go into a pause mode. The LCD display 50 will read as shown in FIG. 12.

In order to set the flow rate, the desired increments 100, 10 and 1 are entered into the microcontroller by depressing the appropriate keys 331 through 333. In order to advance the numbers on the display 55, each key is touched. In the preferred embodiment, if a key is held, the numbers will roll forward on the display approximately one unit every one-half second automatically.

Figure 13:
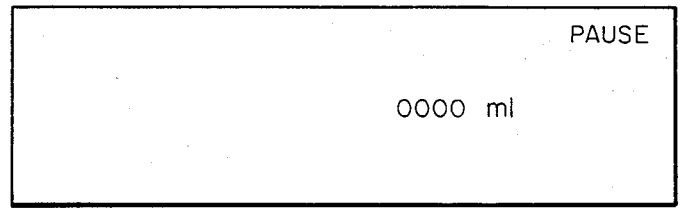

Upon touching the key associated with the volume to be delivered, the display 50 will read as shown in FIG. 13. The volumetric controller is still in the pause mode. The volume to be delivered is set in the same way as the flow rate. When this has been accomplished, the start button is pressed and the green light 340 will appear and flash with each drop of fluid indicating that the unit is operating. The roller clamp 36 should be opened immediately after the start button is pushed.

Whenever the pause button is touched, the volumetric controller stops infusion. The red light 342 flashes intermittently and the volumetric controller emits an audible beep approximately every two secondd to remind the operator that the volumetric controller is not infusing. If the start button is not pressed within a predetermined period of time, then the volumetric controller will sound alarm 58. Touching the pause again will give the operator a predetermined period of time, for example, two more minutes, of intermittent beeps and silence of the audible alarm.

In order to check the volume infused, the buttom marked "VI" is depressed. The display 50 will give the volume infused in milliliters. To reset the volume infused to zero milliliters, the pause button is depressed. Then, the VI button is pressed and held for a predetermined period of time.

Figure 14:
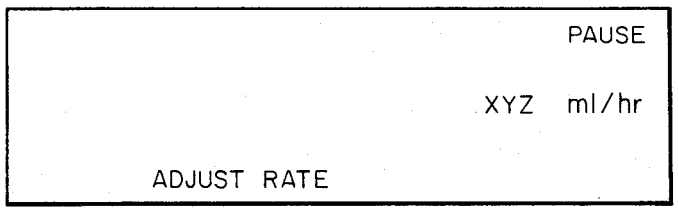

To change the rate, the button "CR" is depressed, the unit is in pause, and the display will read as shown in FIG. 14. The new rate is entered in the same way as the initial rate was set as described hereinbefore. In order to cause the volumetric controller to operate at the new rate, the start button is then depressed.

Figure 15:
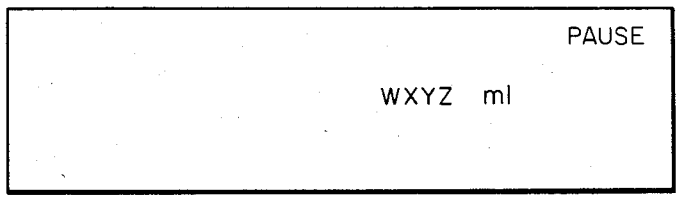

To change the volume to be delivered, the pause button is depressed to place the microcontroller in a pause situation. Next, the volume to be delivered button is depressed and the display will read as shown in FIG. 15. The new volume may then be entered in the manner described hereinbefore with the start button depressed to reactivate the volumetric controller.

Figure 16:
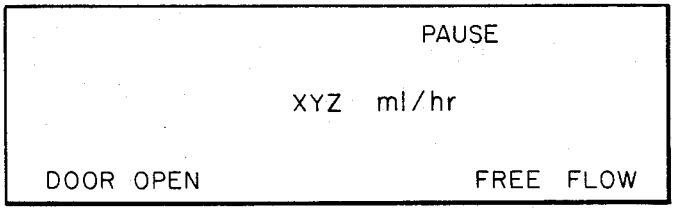

To change the sensing chamber 44, IV tubing, or to discontinue the operation, the pause button is depressed. Next, the roller clamp 36 is closed on the IV tubing 32. The pause button is then touched twice and the door 306 is opened. The display 50 will read as shown in FIG. 16.

The drop volume sensing chamber 44 may then be removed. If a new chamber is used, the procedure outlined hereinbefore for purging and filling of the sensing chamber should be followed. The door is then closed and the start button is then pressed to reactivate the controller. If the IV operation is to be discontinued, then, after the door is closed, the volumetric controller is merely turned off.

In order to change the IV solution container 30, the volumetric controller 10 is placed into a pause state. The empty IV solution is then removed and replaced in a conventional manner.

Also associated with the volumetric controller are a series of sensors and an associated alarm, which measure rate variation, air in-line, door open, low battery, free flow, and infusion complete.

Whenever the volumetric controller senses one of these alarm conditions, with the exception of infusion complete, an audible and visual alarm is activated and the display 50 tells the reason for the alarm. The audible alarm 58 can be silenced by touching the pause button. The visual alarm 342 continues to flash a red light and beep at predetermined intervals with each light.

Also associated with the display 50 is a back light 250 formed from an electroluminescent lamp that is powered by a voltage amplifier 352. When ambient light is below a certain level, as sensed by sensor 55, the microcontroller issues a signal on line 254 which causes a Schmitt trigger 356 and field effect transistor pair 358 to activate the amplifier 352 and provide 200 volts to the lamp 350.

In the preferred embodiment, when the volume infused is equal to the preset volume to be delivered, the flow control will alarm and switch the flow rate to a 5 milliliter per hour keep open rate and continue to infuse at this new rate.

When the flow rate varies greater than the control range of the volumetric controller 10, an audible and visual alarm is activated, and the volumetric controller automatically stops infusion. To silence the alarm, the pause button is touched.

When air is present in the IV tubing, the volumetric controller stops the infusion and gives an audible and visual alarm. The alarm is silenced by pressing the pause button. If the volumetric controller door is open when the controller is operating, the controller will give an audible and visual signal. Approximately one hour before the battery life is depleted the volumetric controller will stop the infusion and give an audible and visual alarm. If no action is taken within a predetermined period of time, the microcontroller will shut down.

Having described the subject invention in the context of the volumetric controller, the subject invention as embodied in a urinary monitor will now be described.

Figure 17:
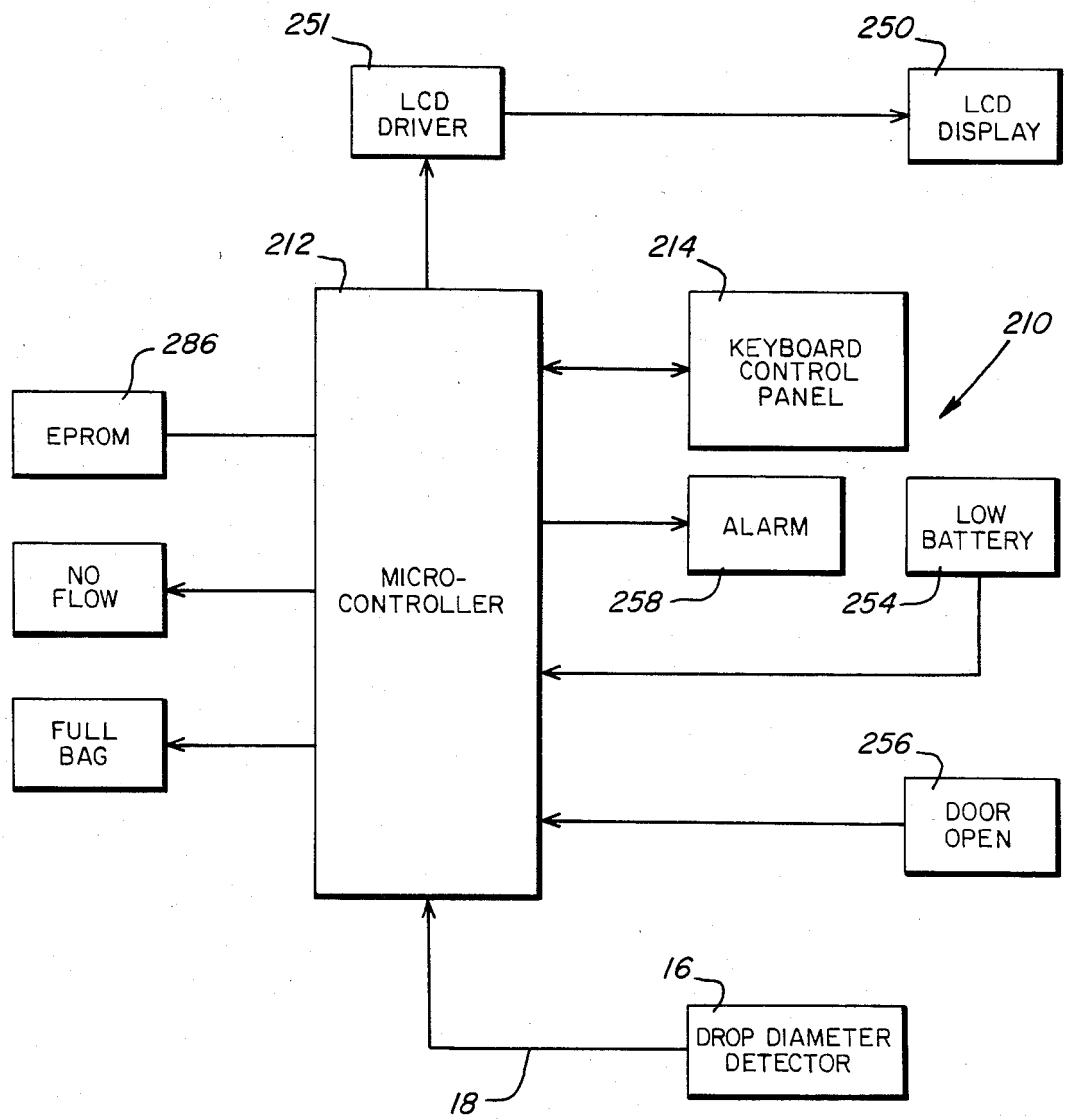
FIG. 17 is a block diagram showing the major components of an embodiment of a unitary output monitor employing the teachings of the subject invention.

The basic elements constituting the urinary output monitor are collectively designated as 210 in FIG. 17. At the heart of the urinary output monitor is a microcontroller 212. In a preferred embodiment, the microcontroller is a ROMless microcontroller (such as that carrying product identification No. COP404LS, as manufactured by National Semiconductor) used with an auxiliary EPROM 286. It is to be understood, however, that the ROMless microcontroller and its auxiliary EPROM could be replaced by any conventional microcontroller with internal ROM. A keyboard control panel 214 is provided to place information into the microcontroller 212. The control panel is used to provide certain commands to the microcontroller, such as start, display measured volume, display elapsed time, etc.

Also forming part of the urinary output monitor is the novel drop diameter detector 16, which has already been described. The detector 16 provides information to the microcontroller on lines 18. The information is in the nature of a signal representative of the presence and a function of the diameter of urine drops as they pass through the urine monitor.

The urinary output monitor is intended to be used as part of a urine collection system. With reference to FIG. 19, a diagrammatic illustration of a urine collection system according to the present invention is presented. Basically, the system comprises a catheter 242 with one end (not shown) being inserted into the patient. The other end 230 of the catheter is secured in a conventional manner as by friction or adhesive to the top of drop volume detecting chamber 244 forming part of the drop diameter detector 16. The bottom of the chamber 244 is secured, again as by friction or adhesive, to a bag 247 or other suitable container by way of tube 246 for collecting the urine passed by the patient. As drops of urine pass through the drop volume chamber 244, their presence and duration are detected by the urinary output monitor 210.

Returning to FIG. 17, in order to enable the user to determine the type of information being entered by the keyboard control panel into the microcontroller, an LCD (liquid crystal display) 250 driven by an appropriate LCD driver 251 under signals generated by the microcontroller is provided.

Finally, certain protective features, such as a low battery detector 254, and a door open detector 256 are provided. Each of these detectors provides information to the microcontroller 212, which in turn activates an alarm 258.

Figure 23:
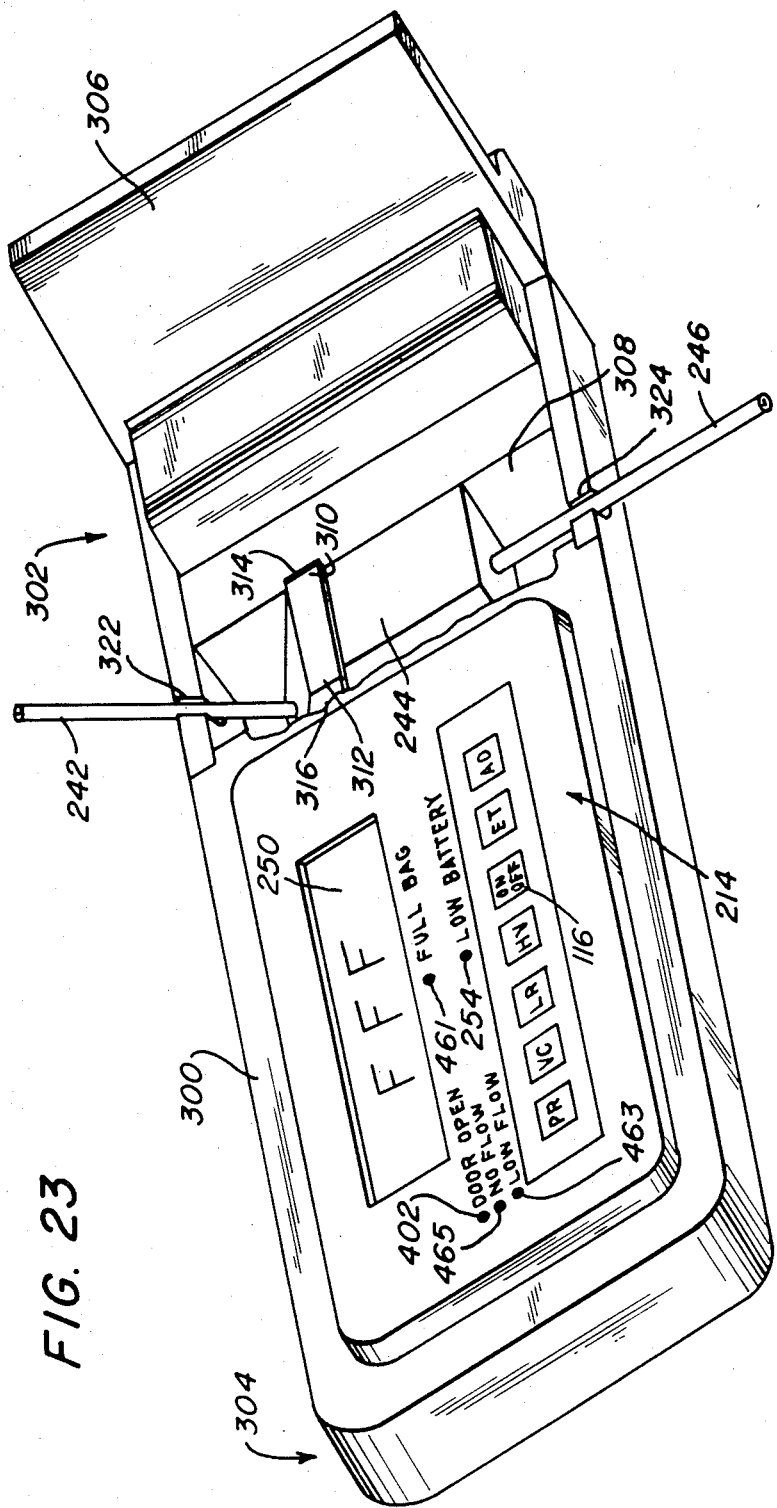
FIG. 23 is a perspective view of the front of an instrument forming part of the urinary output monitor.
Figure 24:
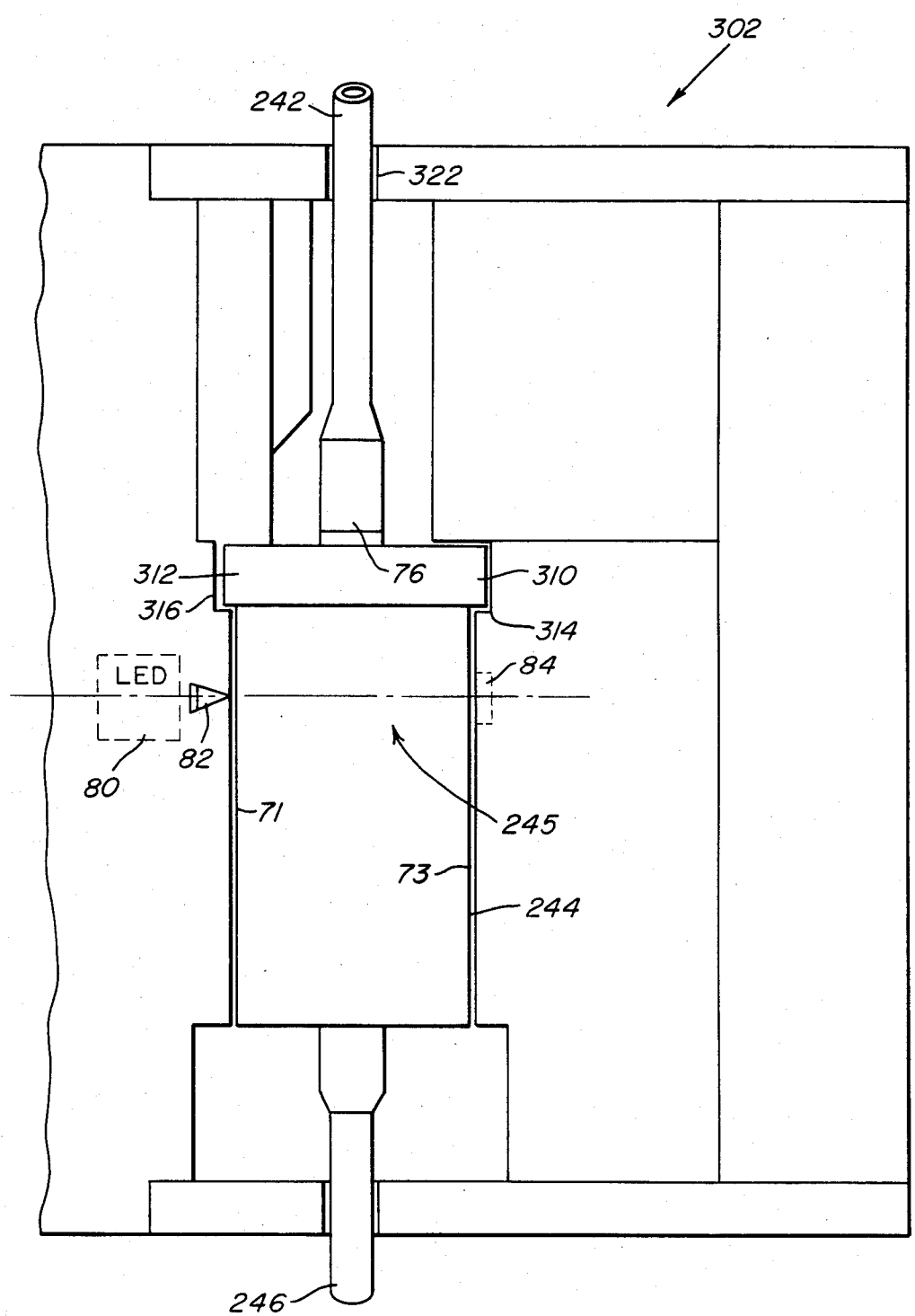
FIG. 24 is a front view of the sensing chamber receiving portion of the urinary output monitor with a sensing chamber mounted therein.

With reference to FIGS. 20 through 24, the details of the sensing chamber 244 will now be described. In its position of intended use, as shown in FIGS. 21 and 24, one embodiment of the sensing chamber 244 is the same (like elements being denoted by like reference numerals) as that previously described with regard to the volumetric controller with the following exceptions. As in the volumetric controller, the sensing chamber 244 possesses four vertically oriented walls 61 through 64. Each of the walls has associated with it the periphery of one of the sides of the square cross section. As constructed, walls 61 and 63 are oriented generally parallel to each other as are walls 62 and 64. The interior surfaces of each wall are generally curved to define one of the four lenses 71, 73, 75 and 77. However, the sensing chamber 244 does not contain the four splash walls 361 as are found in the sensing chamber 44. The bottom 66 of the chamber 244 contains centrally located aperture 68. Emanating downwardly from the aperture is hollow projection 70. The projection 70 is secured to one end of the PVC tubing 46 to provide fluid communication between that tube and the urine collection bag 247.

In an alternative embodiment (FIGS. 20 and 23), at the top portion of the chamber 244, there is provided a cover plate or cap 272 which is canted at a 30° angle with respect to the cross-sectional plane of the sensing chamber. The interior of the cap defines the final surface constituting the interior volume 45 of the chamber 244. Located off to one side on the cap is an aperture 274. Protruding upwardly at a 60° angle from the aperture is a hollow projection 76. This projection is connected to one end of catheter 242 to create a fluid communication between the interior of the sensing chamber 44 and the catheter.

With reference to FIGS. 23 and 24, the details of the structure which houses the urinary output monitor will now be described. The structure is similar to the housing for the volumetric controller; thus like reference numerals denote like elements. A housing 300 is generally divided into two portions. As oriented in FIG. 23, the right-hand side 302 of the housing provides a general area for receiving the drop volume chamber 244. The left-hand side 304 of the housing defines a portion for receiving the electronics associated with the operation of the urinary output monitor and also provides the control panel with the keyboard 214 and the display 250.

A door 306 is hingedly mounted and is free to swing back and forth so that in its open position it reveals the cavity 308 within which the drop volume chamber 244 is mounted. In its closed position, the door 306 covers the cavity 308 to secure the drop volume chamber 244 within the cavity 308.

The cavity 308 is configured to accommodate the drop volume chamber 244 in one orientation. This is accomplished by providing keys 310 and 312 at the upper portion of the drop volume chamber 244. These keys mate respectively with keyways 314 and 316 provided in the sidewalls 318 and 320 of the cavity 308. The keyways are fashioned to accommodate both embodiments of the sensing chamber 244 as shown in FIGS. 4 and 8. Channels 322 and 324 are provided at the top and bottom of the chamber 308 to permit insertion of the catheter 242. The back side (not shown) of the body 300 contains a conventional clamp for securing the urinary output monitor housing to the patient's bed.

In use, the sensing chamber 244 is normally positioned as oriented in FIG. 24 within the urinary output monitor. As can be seen in FIG. 23, for the alternative embodiment, the housing and the chamber 244 within it are tilted so that the longitudinal axis of the chamber is at an approximately 30° angle with regard to the vertical axis V. This is done because when the urinary monitor is applied to the bed of a patient, the urinary catheter 242 and the chamber 244 must be lower than the patient. Canting the housing at 30° from the vertical makes it easier for the nurse to visually inspect the operation of the urinary collection system.

When positioned within the urinary output monitor and in use, the infrared LED (light emitting diode) 80 passes a beam of light through a slit 82. The beam of light is then passed through lens 71 and onto lens 73 for reception by phototransistor 84. As can be seen with reference to FIGS. 22 and 24, the lenses are positioned so that they create a series of parallel light rays 86 within the chamber cavity 245.

Having described the details of the sensing chamber, the details of the remaining elements of the urinary output monitor will now be provided.

At the heart of the urinary output monitor 210 is the microcontroller 212. In a preferred embodiment, the microcontroller is the same as that used in the volumetric controller. In order for the user to interface with the microcontroller, a keyboard 214 is provided. The six keys of the keyboard are connected in a conventional manner by lines 281 to six bidirectional I/O (input/output) ports provided in the microcontroller. Through the keyboard, the microcontroller can be given certain commands to start and to display various items. Finally, there is provided a test key for testing and calibration during manufacture. A clock provides a frequency of about 2.09 MHz to run the system oscillator of the microcontroller 212.

Forming part of the urinary output monitor is a memory 286. In a preferred embodiment, the memory is of the same type as used in the volumetric controller. The memory is enabled by a signal received from the microcontroller on line 88.

Eight bidirectional ROM address and data ports provided in the microcontroller to transfer address information and receive data information on lines 90. The address information passes through an 8-bit latch 92 and then into the EPROM via lines 94. The data, on the other hand, is received from the EPROM on lines 96, which merge with lines 90. The microcontroller contains additional ROM address outputs which provide address information to the memory on lines 98.

A door sensor 100 consisting of a light emitting diode which impinges upon a phototransistor is positioned generally in the lower left-hand corner of the receptacle 308. The door sensor 100 is used to provide a signal on line 102 to the microcontroller through a general purpose input 104. A high signal on line 102 indicates that the door of the urinary output monitor is shut. On an output line 400 from the microcontroller, a signal is sent to an LED display 402 to indicate when the door is open.

Forming part of the electrical system for the urinary output monitor is voltage regulator 118 which is a three terminal regulator with 5-volt range and is generally designated as LM78LO5ACZ by National Semiconductor. The output and common ports of the voltage regulator are connected to capacitor C4, whereas the common and the input of the voltage regulator are connected to capacitor C3 and ground. The voltage regulator 118 is used to provide a regulated voltage supply, which in the preferred embodiment is 5 volts. The input of the voltage regulated is connected to the center pole 114 of on/off switch 116. Also connected to the center pole 114 is a green LED 420 which glows when the monitor is running.

In the microcontroller 212, bidirectional I/O port 160 and general purpose output 162 are coupled with general purpose output 142 into the LCD driver 251 which, in turn, produces appropriate signals on lines 166 to activate the LCD display 250.

The final building block of the urinary output monitor is floating trigger 410 similar to that previously described with regard to the volumetric controller. For this reason, like elements bear like reference designations.

As with the volumetric controller, the idea behind the floating trigger in the urinary output monitor is to provide a signal indicative of drop size or drop duration that is independent of changes in the VCE of the phototransistor 84. This is accomplished in the urinary output monitor in same manner as previously described for the volumetric controller.

The output of the phototransistor 84 of the drop diameter detector 16 is fed into the negative input of operational amplifier (op amp) 202 via resistor R6 and capacitor C6. Also, a bias voltage of about +2.0 volts is supplied to the positive input of op amp 200 via resistor R23. The output of op amp 200 is about 2.0 volts and is applied as a bias voltage to the parallel arrangement of capacitor C10 and resistor R16 and into the positive input of op amp 204. The resulting DC voltage is divided between resistors R10 and R16 and appears at the positive input of op amp 202. The information containing the drop duration from drop sensor 16 is AC coupled through resistor R6 and capacitor C6 into the negative input of op amp 202 by the time a trigger voltage level is set through resistors R18 and R20. That trigger voltage, which goes into the negative input of op amp 206, floats so that the pick off point on the AC signal moves up and down in an inverse direction so as to compensate for changes in the VCE of phototransistor 84. In this way, the drop duration is independent of the electronic drift, in general, and VCE drift, in particular.

Figure 18:
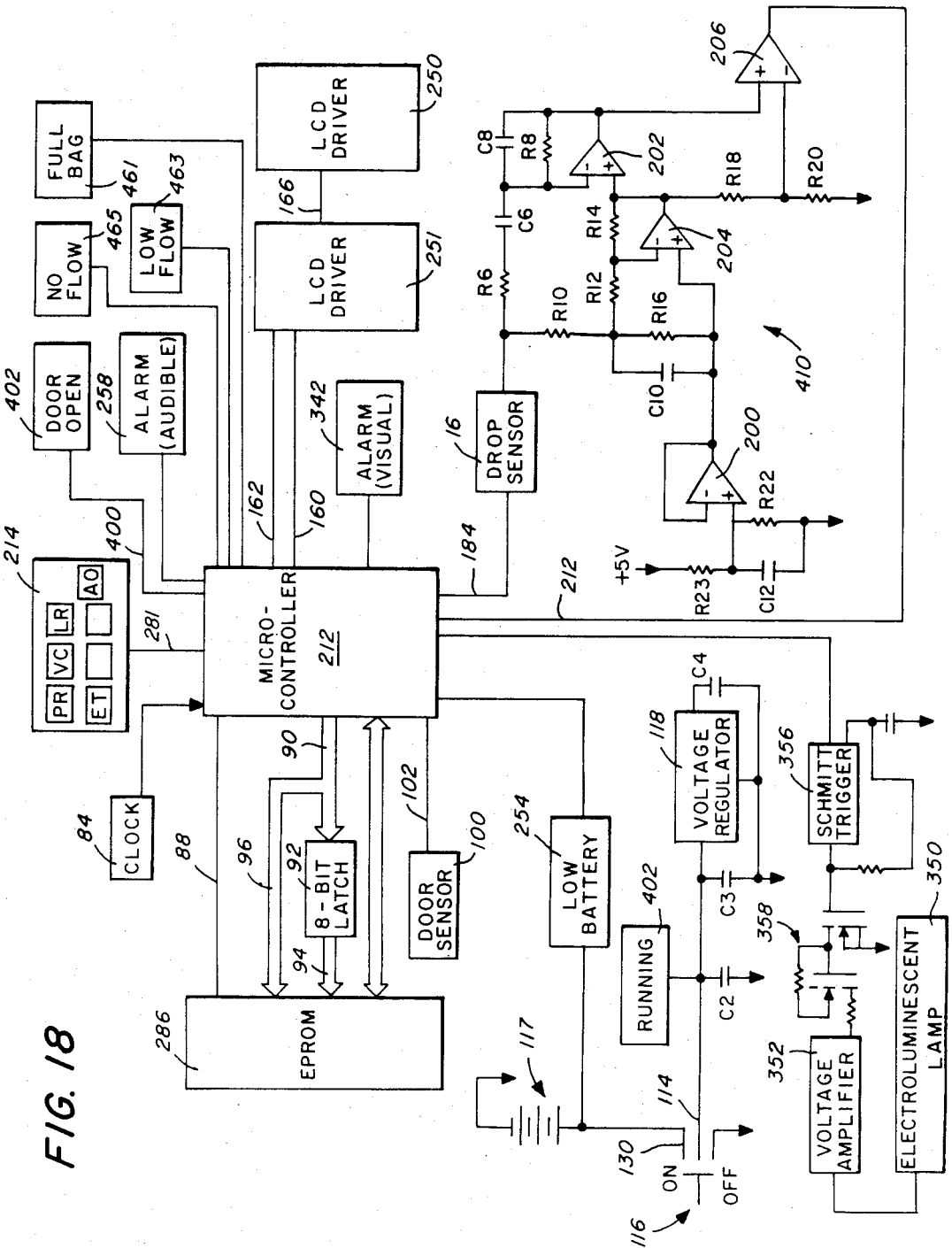
FIG. 18 is a schematic diagram showing the components of the electronic circuitry associated with the urinary output monitor.

Having described the details of the elements constituting the urinary output monitor, the way in which a preferred embodiment of the urinary output monitor produces an accurate measurement of the volume of urine passing the system is as follows. With regard to FIGS. 18, 22 and 24, the light source 80 produces a beam 81 which passes through a slit 82 and through the lens of the drop sensing chamber 244. The lenses 71 and 73 are configured to produce parallel rays 86 within the housing. The light from the LED, after passing through the lenses and slit, is received by a phototransistor 84. The output of the phototransistor is operative with the floating trigger to provide the input signal to the microcontroller. Thus, the light source 80 and the phototransistor 84 with the slit aperture 82 define a plane of light through which the drop of urine passes. As the drop breaks the plane of light, the phototransistor output appears as a rising analog signal as the drop enters the parallel rays of light. The output of the phototransistor remains constant while the drop is contained within the parallel rays of light and gradually drops as the drop leaves the parallel rays of light. This signal is fed into the floating trigger 410 which produces a square wave with a duration in milliseconds proportional to the diameter of the drop of urine. In particular, the output of the floating trigger is high in the absence of a drop of urine and is low as the drop passes through the boundaries defined by the parallel rays of light.

With reference to FIG. 2a, t1 represents the time it takes for a drop of urine to reach a distance L from the orifice O. Time t2 represents the time it takes for that drop to travel a distance equal to its diameter d. Thus, the calculation of drop volume is the same as that previously explained in the context of the volumetric controller.

The square wave signal generated at the output of the floating trigger is approximately 20 milliseconds in duration and is fed to the microcontroller which is able to solve the equation for volume equals $KT^2$.

With reference to FIGS. 19, 23, and 24, the precise operation of a preferred embodiment will now be described. The urine collection system is initially set up by inserting one end of the catheter 242 into the patient with the other end being secured to the top of the sensing chamber 244. The other end of the sensing chamber 244 should then be secured to the tube 246 leading to the urine collection bag 247.

The control keys of the urine monitor are as follows. The Present Hourly Rate key (PR) calls for a display of the urine output rate which is instantaneously, up-dated every 10 minutes. Another key (VC) calls for a display of the total accumulated volume any time urine is flowing through the sensing chamber. The key marked (LR) is the present hour's amount of fluid collected. At the end of the hour period it resets to "0" and starts accumulating again, whereas the Total Accumulated Volume (VC) continues accumulating everything over the last 24 hours. The Last Hours' Volume is the amount of urine that was collected over the most recent hour of the monitor's operation and is stored in the memory 286. The Elapsed Time button (ET) causes a display in minutes and hours.

Switch 116 is placed into the ON position. The display 250 will then read "FFF" as shown in FIG. 23. The door 306 of the unit is then opened. When the door open, the sensing chamber 244 is placed into the receptable 308. Next, the catheter 242 is positioned within the channel 322 above the sensing chamber. The door is then closed. With the door closed, the urine monitor will go into a pause mode and then begin normal operation.

The actual operation of the urine output monitor 210 is as follows. The present rate is always displayed on display 250 in mls per hour except if the monitor is in a Volume Collected mode. Under any circumstances, the display is updated every 10 minutes. During the first 10 minutes of operation, the LCD display 250 reads "FFF" ml per hour because there is nothing to update and display during this time interval. At anytime, the total volume collected can be displayed in milliliters (mls) continuously when the key marked (VC) is touched by the operator. Likewise, elapsed time is displayed when the key marked (ET) is touched. The display is in hours and minutes.

The key marked (LR) causes the last hours rate to be displayed in ml per hour. The monitor operates 60 minutes before each hourly rate is updated. The monitor switches back to display the present rate five seconds after a key has been touched and released.

Optionally, inside the disposable chamber 244 are placed three tiny plastic balls 451–453, each ball having a different specific gravity. When urine is present in the chamber 244, one, two or three balls may float or sink depending on the specific gravity of the urine. The range of specific gravities in the urine that is clinically important is between 1.000 and 1.040. One of the three balls has a specific gravity of 1.010. A second ball has a specific gravity of 1.020, and the third ball has a specific gravity of 1.030. Hence, the nurse need only open up the chamber door and look into the disposable sensing chamber 244 and to see which of the three balls is floating or sinking and therefore be able to determine the specific gravity of the urine. Through the use of the three balls, this particular parameter, specific gravity, is easily observed and obviates the need to handle the urine, and also prevents spilling of urine. The reason specific gravity is important is, if a patient's urine is, for example, 1.005, the clinician may elect to put more salt into the intravenous solutions. If the specific gravity is 1.040 then the physician would elect to give more "salt-free" water to the patient. Therefore, specific gravity measurements give an indication of the state of dilution in the patient.

Also associated with the urinary output monitor are a series of sensors and an associated alarm 258, which measure door open 402, and low battery 254. Also, there are LED displays to indicate full bag 461, low flow 463, and no flow 465.

Whenever the urinary output monitor senses one of these alarm conditions, an audible alarm 258 and visual alarm 342 are activated and the display 250 tells the reason for the alarm. The audible alarm 258 can be silenced by touching the alarm off key (AO). The visual alarm 342, in the form of an LED, continues to flash a red light and the audible alarm beeps at predetermined intervals until the condition is corrected.

If the output of urine from the patient falls below 30 mls per hour or if the urine system is constricted to reduce urine flow, low flow urine output monitor alarms and flashes a "Lo". The audible alarm can be extinguished. Similarly a "No flow" alarm sounds and LED comes on if flow is less than 3 mls per hour. This alarm can be extinguished also. The "door open" alarm is a 4 minute alarm (it is both audible and has a red LED). This alarm can be extinguished but will re-alarm in 4 minutes if the "door open" situation has not been corrected. When a "full bag" or full chamber of 2000 ml occurs, an audible and visual alarm is activated. "Low battery" alarms are both audible and visual.

From the above, it is apparent that many modifications and variations of the present invention are possible in light of the above teachings. It is, therefore, to be understood that, within the scope of the appended claims, the invention may be practiced otherwise than as specifically described.

What is claimed is:

1. A gravity intravenous administration system for administering an IV solution from an IV container, said system comprising:
   (A) means for storing an IV solution to be administered;
   (B) a sensing chamber including
      (a) a hollow housing made up of a plurality of vertically extending wall portions defining a hollow cavity,
      (b) orifice means for introducing IV solution as a series of drops into said cavity, said orifice means oriented so that said drops under gravity pass through said cavity,
      (c) first and second of said wall portions arranged opposite each other,
      (d) first lens means defined on said first wall portion,
      (e) second lens means defined on said second wall portion, said first and second lens means arranged relative to each other to cause a light beam passing through them to be arranged as a series of parallel light rays within said cavity and defining a plane generally perpendicular to the path defined by the passing drops; and
   (C) means for placing the IV container in fluid communication with said orifice means.

2. The gravity intravenous administration system of claim 1, further comprising:
   means for producing a light beam;
   means for directing said light beam through said first lens means; and
   means for receiving said light beam after it passes through said second lens means and for producing a signal proportional to the intensity of said light beam after it passes through said second lens means.

3. The gravity intravenous administration system of claim 1 further comprising controlling means for controlling at least one of the size of the drops and interval between drops from said orifice means.

4. The gravity intravenous administration system of claim 3, wherein said controlling means comprises a flexible tube, the cross section of which is altered.

5. The gravity intravenous administration system of claim 4, further comprising anvil means touching an exterior portion of said tubing;
   movable plunger means positioned opposite said anvil means with said tubing being interposed therebetween;
   said plunger being operable to move toward and away from said anvil to alter the cross section of said tubing.

6. The gravity intravenous administration system of claim 5, further comprising stepper motor means for causing said plunger to move in a desired direction in predetermined increments.

7. The gravity intravenous administration system of claim 4, further comprising means for receiving said signal;
   means for evaluating said signal to determine the precise volume of the drop as it passes through said plane of parallel light rays; and
   altering means responding to said signal for altering the cross section of said tubing.

8. The gravity intravenous administration system of claim 7, wherein said altering means alters the interval between drops.

9. The gravity intravenous administration system of claim 7, wherein said altering means maintains the time interval between drops constant while altering the volume of the individual drops.

10. For use in a gravity intravenous administration system, a drop sensing chamber, said chamber comprising:
    a hollow housing made up of a plurality of vertically extending wall portions defining a hollow cavity;
    orifice means for introducing an IV solution as a series of drops into said cavity, said orifice means oriented so that said drops under gravity pass through said cavity;
    first and second of said wall portions arranged opposite each other;
    first lens means defined on said first wall portion; and
    second lens means defined on said second wall portion, said first and second lens means arranged relative to each other to cause a light beam passing through them to be arranged as a series of parallel light rays within said cavity and defining a plane generally perpendicular to the path defined by the passing drops.

11. An intravenous administration system comprising:
    a drop detection chamber;

sensing means for sensing the passage of drops of IV solution through said chamber;

a flexible tubing having one end in fluid communication with said chamber and the other end adapted to be connected in fluid communication with a source of IV solution, said one end of said tubing defining a drop former within said chamber;

actuator means responsive to control signals for constricting and opening the hollow interior of said flexible tubing; and control means for issuing said control signals to cause said actuator means to operate in such fashion that, while the system is administrating IV solution, said hollow interior is never completely constricted, but is closed only to such an extent that internal friction within the tube just prevents the formation of additional drops at said drop former within said chamber.

12. The system of claim 11, further comprising means in fluid communication with said drop chamber for introducing said IV solution into the body of a user.

13. The system of claim 12, further comprising detecting means for detecting an abnormality in the flow of IV solution through said system and for issuing a signal indicative of that abnormality, said control means being responsive to said signal issued by said detecting means for causing said actuator to constrict said flexible tubing.

14. The system of claim 13, wherein said abnormality is air in said system.

15. In an intravenous administration system having a drop detection chamber, an apparatus for controlling the passage of drops of IV solution through the chamber, said apparatus comprising:

sensing means for sensing the passage of said drops of IV solution through said chamber;

a flexible tubing having one end in fluid communication with said chamber and the other end adapted to be connected in fluid communication with a source of IV solution, said one end of said tubing defining a drop former within said chamber;

actuator means responsive to control signals for constricting and opening the hollow interior of said flexible tubing; and control means for issuing said control signals to cause said actuator means to operate in such fashion that, while the system is administrating IV solution, said hollow interior is never completely constricted, but is closed only to such an extent that internal friction within the tube just prevents the formation of additional drops at said drop former within said chamber.

16. The apparatus of claim 15, wherein, prior to the administration of IV solution, a first control signal issued by said control means causes said actuator means to completely constrict said flexible tubing.

17. The apparatus of claim 16, wherein a second control signal issued by said control means causes said actuator means to release the constriction of said flexible tubing in predetermined amounts until a drop is detected by said sensing means.

18. The apparatus of claim 17, wherein further control signals are issued by said control means for causing said actuator means to constrict and open the hollow interior of said flexible tubing to produce drops of varying sizes within said chamber.

19. The apparatus of claim 17, wherein further control signals are issued by said control means for causing said actuator means to constrict and open the hollow interior of said flexible tubing to produce drops at varying time intervals within said chamber.

20. The intravenous administration system of claim 11, further comprising:

first means adapting said intravenous administration system to be powered by a remote source of power;

an internal source of power; and means responsive to the interruption of the delivery of power to said system for causing said internal source of power to provide an electrical control signal to said actuator for stopping the flow of drops through said chamber.

21. A flow monitor, said monitor comprising:

a drop chamber for observing the passage of solution from a source to a collection site, said drop chamber including means for introducing said solution into said chamber as a series of drops;

producing means for producing a light beam;

means for directing said light beam through said chamber;

receiving means for receiving said light beam after it passes through said chamber and for issuing a drop volume signal indicative of the volume of a drop passing through said chamber, said producing and receiving means each subject to electronic drift; and means for compensating said drop volume signal for electronic drift introduced by said producing and receiving means.

22. A flow monitor for measuring precise volumes of fluid, said monitor comprising:

a sensing chamber including a hollow housing made up of a plurality of vertically extending wall portions defining a hollow cavity;

orifice means for introducing fluid as a series of drops into said cavity, said orifice means oriented so that said drops under gravity pass through said cavity;

first and second of said wall portions arranged opposite each other;

first lens means defined on said first wall portion; and second lens means defined on said second wall portion, said first and second lens means arranged relative to each other to cause a light beam passing through them to be arranged as a series of parallel light rays within said cavity and defining a plane generally perpendicular to the path defined by the passing drops.

23. The flow monitor of claim 22, further comprising:

means for producing a light beam;

means for directing said light beam through said first lens means; and means for receiving said light beam after it passes through said second lens means and for producing a signal proportional to the intensity of said light beam after it passes through said second lens means.

24. The flow monitor of claim 23, further comprising;

means for receiving said signal;

means for evaluating said signal to determine the precise volume of the drop as it passes through said plane of parallel light rays.

25. An intravenous administration system comprising:

a drop detection chamber;

sensing means for sensing the passage of drops of IV solution through said chamber;

measuring means for measuring the volume of drops sensed by said sensing means;

means for determining whether the volume of each drop as measured by said measuring means is within a predetermined range of drop volumes;

a flexible tubing having one end in fluid communication with said chamber and the other end adapted to be connected in fluid communication with a source of IV solution;

actuator means responsive to control signals for altering the cross-sectional size of the hollow interior of said flexible tubing;

drop forming means for forming drops which are introduced into said drop detection chamber for passage past said sensing means, the size of the formed drops being proportional to the size of the cross-section of said flexible tubing;

control means for issuing said control signals to cause said actuator means to alter the cross-section of said flexible tubing in such fashion that, while the system is administrating IV solution, the time interval between drops is altered when the volume of the measured drops is within said predetermined range and the volume of said drops is altered when the volume of the measured drops is outside of said predetermined range.

26. For use in a flow monitor for measuring precise volumes of fluid, a drop sensing chamber, said chamber comprising:

a sensing chamber including a hollow housing made up of a plurality of vertically extending wall portions defining a hollow cavity;

orifice means for introducing fluid as a series of drops into said cavity, said orifice means oriented so that said drops under gravity pass through said cavity;

first and second of said wall portions arranged opposite each other;

first lens means defined on said first wall portion; and second lens means defined on said second wall portion, said first and second lens means arranged relative to each other to cause a light beam passing through them to be arranged as a series of parallel light rays within said cavity and defining a plane generally perpendicular to the path defined by the passing drops.

* * * * *